US010683382B2

(12) United States Patent
Kai et al.

(10) Patent No.: US 10,683,382 B2
(45) Date of Patent: Jun. 16, 2020

(54) COPOLYMER COMPRISING A LIGNIN OR LIGNIN DERIVATIVE AND A POLY(ALKYLENE OXIDE) ALKYL ETHER (METH)ACRYLATE, AND A HYDROGEL COMPRISING THE COPOLYMER

(71) Applicant: AGENCY FOR SCIENCE, TECHNOLOGY AND RESEARCH, Singapore (SG)

(72) Inventors: Dan Kai, Singapore (SG); Xian Jun Loh, Singapore (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 36 days.

(21) Appl. No.: 15/552,262

(22) PCT Filed: Feb. 18, 2016

(86) PCT No.: PCT/SG2016/050085
§ 371 (c)(1),
(2) Date: Aug. 18, 2017

(87) PCT Pub. No.: WO2016/133466
PCT Pub. Date: Aug. 25, 2016

(65) Prior Publication Data
US 2018/0030192 A1 Feb. 1, 2018

(30) Foreign Application Priority Data
Feb. 18, 2015 (SG) .......................... 10201501261Q

(51) Int. Cl.
*C08F 290/06* (2006.01)
*A61L 27/52* (2006.01)
(Continued)

(52) U.S. Cl.
CPC .......... *C08F 290/062* (2013.01); *A61L 27/18* (2013.01); *A61L 27/26* (2013.01);
(Continued)

(58) Field of Classification Search
CPC .................................................... C08F 290/062
See application file for complete search history.

(56) References Cited

U.S. PATENT DOCUMENTS 5,194,552 A * 3/1993 Meister ................. C08F 289/00
525/8
2007/0260046 A1* 11/2007 Tomita ................ B01F 17/0028
530/500

FOREIGN PATENT DOCUMENTS

CN          102418548 A      4/2012
CN          103723944 A      4/2014
(Continued)

OTHER PUBLICATIONS

Diao et al. (RSC Adv. 2014, 4, 42996) (Year: 2014).*
PCT Notification of Transmittal of the International Search Report and the Written Opinion of the International Searching Authority, or the Declaration for PCT Counterpart Application No. PCT/SG2016/050085 Containing International Search Report, 15 pgs. (dated Apr. 22, 2016).
(Continued)

*Primary Examiner* — Michael F Pepitone
(74) *Attorney, Agent, or Firm* — Womble Bond Dickinson (US) LLP

(57) ABSTRACT

A copolymer comprising an oxygenated polyaromatic alcohol and a poly (alkylene oxide) alkyl ether (meth)acrylate is disclosed, wherein the oxygenated polyaromatic alcohol is preferably lignin or lignin derivative. A hydrogel comprising the copolymer and a cyclic oligosaccharide such as α-cyclodextrin is also disclosed, which can be used in biomedical or personal care industries, for example as a carrier for an active agent.

19 Claims, 21 Drawing Sheets

(51) Int. Cl.
  *C08F 220/28* (2006.01)
  *C08F 293/00* (2006.01)
  *A61L 27/18* (2006.01)
  *C08F 2/38* (2006.01)
  *C08L 5/16* (2006.01)
  *C08L 97/00* (2006.01)
  *C08H 7/00* (2011.01)
  *A61L 27/26* (2006.01)
  *C08G 83/00* (2006.01)
  *C08L 71/02* (2006.01)

(52) U.S. Cl.
  CPC ............... *A61L 27/52* (2013.01); *C08F 2/38* (2013.01); *C08F 220/28* (2013.01); *C08F 290/06* (2013.01); *C08F 293/005* (2013.01); *C08G 83/003* (2013.01); *C08G 83/005* (2013.01); *C08H 6/00* (2013.01); *C08L 5/16* (2013.01); *C08L 71/02* (2013.01); *C08L 97/00* (2013.01); *C08F 2220/286* (2013.01); *C08F 2438/01* (2013.01); *C08L 2203/02* (2013.01)

(56) References Cited

FOREIGN PATENT DOCUMENTS

WO    WO 2016/028230 A1    2/2016
WO    WO-2016028230 A1 *   2/2016   ............... G08H 6/00

OTHER PUBLICATIONS

Bishuo Diao, et al., "Biomass-based thermogelling copolymers consisting of lignin and grafted poly(Nisopropylacrylamide), poly-(ethylene glycol), and poly(propylene glycol)," RSC Adv., vol. 4, No. 81, pp. 42996-43003 (Sep. 11, 2014).

Zhen Ping Sun, et al., "Polycarboxylate-Lignosulfonate Copolymerized High Performance Water Reducing Agent: Preparation and Application," Advanced Materials Research, vol. 687, pp. 435-442 (Apr. 30, 2013).

Dani Kai, et al., "Development of Lignin Supramolecular Hydrogels with Mechanically Responsive and Self-Healing Properties," ACS Sustainable Chem. Eng., vol. 3, No. 9, pp. 2160-2169 (Jul. 24, 2015).

Dani Kai, et al., "Towards lignin-based functional materials in a sustainable world," Green Chem., vol. 18, No. 5, pp. 1175-1200 (Jan. 8, 2016).

Kerh Li Liu, et al., "Supramolecular hydrogels based on cyclodextrin-oolymer polypseudorotaxanes: materials design and hydrogel properties," Soft Matter, vol. 7, No. 24, pp. 11290-11297 (Oct. 5, 2011).

IP Office of Singapore, Written Opinion of Counterpart Singapore Patent Application No. 11201706688X, dated Apr. 28, 2018, 8 pgs.

PCT International Preliminary Report on Patentability for PCT Application No. PCT/SG2016/050085, 8 pgs. (dated Aug. 22, 2017).

* cited by examiner

COPOLYMER COMPRISING A LIGNIN OR LIGNIN DERIVATIVE AND A POLY(ALKYLENE OXIDE) ALKYL ETHER (METH)ACRYLATE, AND A HYDROGEL COMPRISING THE COPOLYMER

CROSS-REFERENCE TO RELATED APPLICATIONS

This patent application is a U.S. National Phase Application under 35 U.S.C. § 371 of International Application No. PCT/SG2016/050085, filed on 18 Feb. 2016, entitled A COPOLYMER COMPRISING A LIGNIN OR LIGNIN DERIVATIVE AND A POLY(ALKYLENE OXIDE) ALKYL ETHER (METH)ACRYLATE, AND A HYDROGEL COMPRISING THE COPOLYMER, which claims priority to Singapore application No. 10201501261Q, filed on 18 Feb. 2015.

TECHNICAL FIELD

The present invention generally relates to a copolymer. The present invention also relates to a hydrogel comprising the copolymer.

BACKGROUND ART

Lignin is the second most abundant renewable natural biopolymer on the planet next to cellulose and it is massively generated as a by-product from papermaking and emerging cellulosic ethanol industries. Annually, more than 50 million tons of lignins are produced but only about 2% of the lignins are used in value added applications, including the isolation of chemicals, stabilizing agents and concrete additives, while the rest is used as low grade burning fuel. As fossil fuels are being consumed and their negative influences on environment are increasing, lots of efforts have been put into developing value added materials using lignin to substitute fossil fuel based products due to its abundant availability and renewable resources. On the other hand, the waste lignin provides various advantages, such as adequate reactive groups that can easily be functionalized, high carbon content, low density, being biodegradable and environmentally friendly, antioxidant, antimicrobial, and stabilizer properties, tunable rheological and viscoelastic properties, tailored ability for chemical transformations, continuous production during paper making, high volumes, etc., making it a potential candidate to be used in diverse industrial applications.

Lignin is a randomly cross-linked network biopolymer arising from enzymatic dehydrogenative polymerization of hydroxylated and methoxylated phenylpropane unit, and recently a growing interest has been paid on utilizing lignin's hydrophobic polyol structure to develop novel lignin-based functional materials. However, very few studies have been done on lignin-based hydrogels.

Hydrogel is a class of polymer networks with hydrophilic groups, which enable the absorption of water while remaining resistant to dissolution as the physical or chemical crosslinks formed among their molecules. With the special structure, hydrogels possess various advantages, such as high water content, easy operation, biocompatibility and mechanical properties, and they have been explored for applications in biological medicine, genetic delivery, tissue engineering, and biomedical materials.

Compared to non-injectable chemically crosslinked hydrogels with non-reversible crosslinked structures, physical hydrogels are preferred for biomedical application as they are able to be injected from syringes and allowed to set in the body. Supramolecular hydrogels are physical networks self-assembled by biocompatible gelators with macromolecular or low-molecular-weight molecules via noncovalent interactions, including hydrogen bonding, hydrophobic interactions, host-guest recognition, and crystallization.

However, conventional hydrogels may not be sufficiently strong for the applications that they are used in, may not be able to self-heal when damaged, or may be toxic to a living human or animal body.

There is a need to provide a hydrogel that overcomes, or at least ameliorates, one or more of the disadvantages described above. There is a need to provide a copolymer that can, in one application, be used to form the hydrogel.

SUMMARY OF INVENTION

According to a first aspect, there is provided a copolymer comprising an oxygenated polyaromatic alcohol and a poly (alkylene oxide) alkyl ether (meth)acrylate.

According to a second aspect, there is provided a hydrogel comprising a copolymer having an oxygenated polyaromatic alcohol and a poly (alkylene oxide) alkyl ether (meth) acrylate.

The hydrogel may further comprise a cyclic oligosaccharide. Advantageously, the presence of the oxygenated polyaromatic alcohol in the copolymer may aid in the formation of the hydrogel from a mixture of the copolymer and the cyclic oligosaccharide. Conversely, the inventors had found that a mixture of poly (alkylene oxide) alkyl ether (meth) acrylate and the cyclic oligosaccharide was not able to form a hydrogel, even at high concentrations. Hence, the presence of the oxygenated polyaromatic alcohol in the copolymer and consequently the mixture was necessary to enable a hydrogel to be formed.

The hydrogel may be able to "self-heal" (that is, regain the gel state of the hydrogel after the hydrogel was broken) in a short period of time, as compared to conventional hydrogels (not formed based on the above copolymer with a cyclic oligosaccharide) which can take hours to "self-heal".

According to a third aspect, there is provided a method for forming a hydrogel comprising the step of adding a cyclic oligosaccharide to a copolymer to form a mixture that undergoes gelation to form the hydrogel, wherein the copolymer comprises an oxygenated polyaromatic alcohol and a poly (alkylene oxide) alkyl ether (meth)acrylate

Definitions

The following words and terms used herein shall have the meaning indicated:

The term "copolymer" refers to a combination of at least two polymers, which polymerize or cross-link with each other to form the copolymer. The copolymer may be a block copolymer, an alternating copolymer, a random copolymer, a graft copolymer, a brush copolymer, a linear copolymer, a branched copolymer or the like.

The term "hydrogel" is used in the conventional sense to refer to a water-swellable polymeric system that can absorb a substantial amount of water to form an elastic gel.

The term "storage modulus" is used herein as an indicator that characterizes the stiffness of the hydrogel. The storage modulus is the tendency of the hydrogel to be deformed elastically when a force is applied to it.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a copolymer will now be disclosed.

The copolymer comprises an oxygenated polyaromatic alcohol and a poly (alkylene oxide) alkyl ether (meth)acrylate.

The molecular weight of the copolymer may be in the range of about 5,000 g/mol to about 500,000 g/mol, about 5,000 g/mol to about 10,000 g/mol, about 5,000 g/mol to about 100,000 g/mol, about 5,000 g/mol to about 200,000 g/mol, about 5,000 g/mol to about 300,000 g/mol, about 5,000 g/mol to about 400,000 g/mol, about 10,000 g/mol to about 500,000 g/mol, about 100,000 g/mol to about 500,000 g/mol, about 200,000 g/mol to about 500,000 g/mol, about 300,000 g/mol to about 500,000 g/mol, about 400,000 g/mol to about 500,000 g/mol, or about 10,000 g/mol to about 200,000 g/mol.

The copolymer may have a polydispersity of at least 1, at least 1.1, at least 1.2, at least 1.23, at least 1.24 or at least 1.3.

The copolymer may have a melting temperature of about 32° C. to about 36° C., about 32° C. to about 33° C., about 32° C. to about 34° C., about 32° C. to about 35° C., about 33° C. to about 36° C., about 34° C. to about 36° C., or about 35° C. to about 36° C.

The copolymer may have a degradation temperature of about 350° C. to about 370° C., about 350° C. to about 355° C., about 350° C. to about 360° C., about 350° C. to about 365° C., about 355° C. to about 370° C., about 360° C. to about 370° C. or about 365° C. to about 370° C.

The copolymer may have about 5 to about 1,000, about 5 to about 30, about 5 to about 60, about 10 to about 1,000, about 100 to about 1,000, about 500 to about 1,000, about 5 to about 10, about 30 to about 1,000, about 60 to about 1,000, about 5 to about 100, about 5 to about 500, or about 30 to about 60 molecules of poly (alkylene oxide) alkyl ether (meth)acrylate bound to each molecule of the oxygenated polyaromatic alcohol.

The oxygenated polyaromatic alcohol may be a lignin or a lignin derivative. The lignin may include lignin, steam explosion lignin, acid hydrolysis lignin, lignosulfonate, soda lignin or organosolv lignin. The lignin derivative may include lignin esters, lignin ethers, carboxy lignins, hydroxyalkylated lignin, acylated lignin or hydroxyalkoxy lignins. More specifically, the lignin derivatives include lignin acetate, lignin propionate, lignin butyrate, lignin ethyl ether, lignin methyl ether, carboxymethyl lignin, (hydroxyethoxy) lignin, or (hydroxypropoxy) lignin.

The oxygenated polyaromatic alcohol may be contained in the copolymer at a weight percentage of about 0.5% to about 90%, about 1% to about 90%, about 5% to about 90%, about 10% to about 90%, about 20% to about 90%, about 30% to about 90%, about 40% to about 90%, about 50% to about 90%, about 60% to about 90%, about 70% to about 90%, about 80% to about 90%, about 0.5% to about 1%, about 0.5% to about 5%, about 0.5% to about 10%, about 0.5% to about 20%, about 0.5% to about 30%, about 0.5% to about 40%, about 0.5% to about 50%, about 0.5% to about 60%, about 0.5% to about 70%, about 0.5% to about 80%, or about 2% to about 50%.

The molecular weight of the oxygenated polyaromatic alcohol may be in the range of about 5,000 g/mol to about 100,000 g/mol, about 5,000 g/mol to about 10,000 g/mol, about 5,000 g/mol to about 20,000 g/mol, about 5,000 g/mol to about 30,000 g/mol, about 5,000 g/mol to about 40,000 g/mol, about 5,000 g/mol to about 50,000 g/mol, about 5,000 g/mol to about 60,000 g/mol, about 5,000 g/mol to about 70,000 g/mol, about 5,000 g/mol to about 80,000 g/mol, about 5,000 g/mol to about 90,000 g/mol, about 10,000 g/mol to about 100,000 g/mol, about 20,000 g/mol to about 100,000 g/mol, about 30,000 g/mol to about 100,000 g/mol, about 40,000 g/mol to about 100,000 g/mol, about 50,000 g/mol to about 100,000 g/mol, about 60,000 g/mol to about 100,000 g/mol, about 70,000 g/mol to about 100,000 g/mol, about 80,000 g/mol to about 100,000 g/mol, about 90,000 g/mol to about 100,000 g/mol, or about 25,000 g/mol to about 30,000 g/mol. The molecular weight may be about 28,000 g/mol.

The molar mass of the oxygenated polyaromatic alcohol may be in the range of about 1,000 g/mol to about 50,000 g/mol, about 1,000 g/mol to about 10,000 g/mol, about 1,000 g/mol to about 20,000 g/mol, about 1,000 g/mol to about 30,000 g/mol, about 1,000 g/mol to about 40,000 g/mol, about 10,000 g/mol to about 50,000 g/mol, about 20,000 g/mol to about 50,000 g/mol, about 30,000 g/mol to about 50,000 g/mol, about 40,000 g/mol to about 50,000 g/mol. The molar mass may be about 5,000 g/mol.

The poly (alkylene oxide) alkyl ether (meth)acrylate may be poly (ethylene glycol) methyl ether (meth)acrylate, poly (ethylene glycol) ethyl ether (meth)acrylate, poly (propylene glycol) methyl ether (meth)acrylate, poly (propylene glycol) ethyl ether (meth)acrylate, or mixtures thereof.

The poly (alkylene oxide) alkyl ether (meth)acrylate may be a grafted polymer, a block copolymer, a star polymer, a brush polymer or a hyperbranched polymer.

The average number of alkylene oxide groups in the poly (alkylene oxide) alkyl ether (meth) acrylate may range from 2 to 460, 5 to 460, 10 to 460, 50 to 460, 100 to 460, 150 to 460, 200 to 460, 250 to 460, 300 to 460, 350 to 460, 350 to 460, 400 to 460, 450 to 460, 2 to 5, 2 to 10, 2 to 50, 2 to 100, 2 to 150, 2 to 200, 2 to 250, 2 to 300, 2 to 350, 2 to 400, or 2 to 450.

The molecular weight of the poly (alkylene oxide) alkyl ether (meth)acrylate may be in the range of about 200 g/mol to about 20,000 g/mol, about 200 g/mol to about 500 g/mol, about 200 g/mol to about 1,000 g/mol, about 200 g/mol to about 5,000 g/mol, about 200 g/mol to about 10,000 g/mol, about 200 g/mol to about 15,000 g/mol, about 500 g/mol to about 20,000 g/mol, about 1,000 g/mol to about 20,000 g/mol, about 5,000 g/mol to about 20,000 g/mol, about 10,000 g/mol to about 20,000 g/mol, about 15,000 g/mol to about 20,000 g/mol, or about 1,000 g/mol to 10,000 g/mol.

The molar mass of the poly (alkylene oxide) alkyl ether (meth)acrylate may be in the range of about 100 g/mol to about 8,000 g/mol, about 100 g/mol to about 1,000 g/mol, about 100 g/mol to about 2,000 g/mol, about 100 g/mol to about 3,000 g/mol, about 100 g/mol to about 4,000 g/mol, about 100 g/mol to about 5,000 g/mol, about 100 g/mol to about 6,000 g/mol, about 100 g/mol to about 7,000 g/mol, about 1,000 g/mol to about 8,000 g/mol, about 2,000 g/mol to about 8,000 g/mol, about 3,000 g/mol to about 8,000 g/mol, about 4,000 g/mol to about 8,000 g/mol, about 5,000 g/mol to about 8,000 g/mol, about 6,000 g/mol to about 8,000 g/mol, about 7,000 g/mol to about 8,000 g/mol, or about 1,000 g/mol to about 1,500 g/mol. In one embodiment, the molar mass may be about 1,100 g/mol.

The copolymer may further include a polymer such as polyester, polyurethane, polyamide, polyether, polysaccharide, poly(amino acid)s, polypeptides or proteins.

The copolymer may be prepared via an atom transfer radical polymerization (ATRP) reaction. Generally, the oxygenated polyaromatic alcohol may be functionalized with a halo functionalizing agent to form a macroinitiator (that is, the oxygenated polyaromatic alcohol having surface halo functional groups). The macroinitiator is then reacted with the poly (alkylene oxide) alkyl ether (meth)acrylate in the presence of a catalyst and solvent to form the copolymer.

Hence, there is provided a method for forming a copolymer comprising an oxygenated polyaromatic alcohol and a poly (alkylene oxide) alkyl ether (meth)acrylate, the method comprising the steps of:

a) functionalizing an oxygenated polyaromatic alcohol with a halo functionalizing agent to form a macroinitiator; and b) reacting said macroinitiator with a poly (alkylene oxide) alkyl ether (meth)acrylate in the presence of a catalyst and solvent to form said copolymer.

The halo functionalizing agent may be an agent that introduces a halide moiety on the oxygenated polyaromatic alcohol to form the macroinitiator. The halo functionalizing agent may have a bromo-, chloro-, iodo- or fluoro-group. The halo functionalizing agent may be a halogenated acid halogenide. The halo functionalizing agent may be added to a solution of the oxygenated polyaromatic alcohol under stirring at a cold temperature. The cold temperature may be less than 10° C., or may be around ice conditions (around 0° C.).

The catalyst may be a catalyst that can be used in an ATRP reaction. Typically, the catalyst is a transition metal catalyst.

The transition metal may be exemplarily selected from the group consisting of copper, iron, ruthenium, nickel, osmium, etc. It is to be noted that the type of transition metal catalyst is not limited to those mentioned here, but a skilled person in the art would be aware of any transition metal catalyst that is suitable for use in an ATRP reaction and substitute the mentioned catalyst accordingly.

The solvent may be any solvent that can be used in an ATRP reaction. Typically, the ATRP solvent may be toluene, 1,4-dioxane, xylene, anisole, DMF, DMSO, water, methanol, acetonitrile, etc. It is to be noted that the type of solvent is not limited to those mentioned here, but a skilled person in the art would be aware of any solvent that is suitable for use in an ATRP reaction and substitute the mentioned solvent accordingly.

A specific example of the above process is shown in Scheme 1 below, where the oxygenated polyaromatic alcohol is a lignin (having the structure shown by the first reactant) and the poly (alkylene oxide) alkyl ether (meth) acrylate is a poly(ethylene glycol) methyl ether methacrylate (PEGMA). The halo functionalizing agent is an organic compound having bromide groups such as 2-bromoisobutyryl bromide (BIBB). Here, the lignin is reacted with BIBB to form a lignin macroinitiator having surface bromo functional groups. The lignin macroinitiator then reacts with PEGMA in the presence of a catalyst to form the lignin-PEGMA copolymer.

Scheme 1

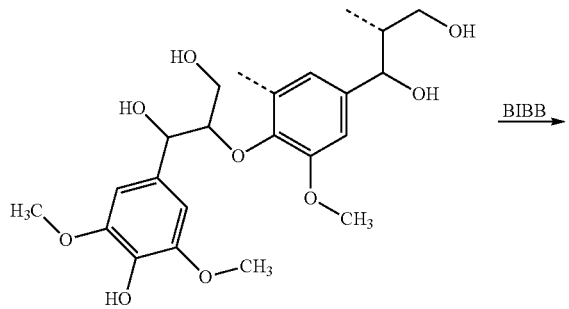

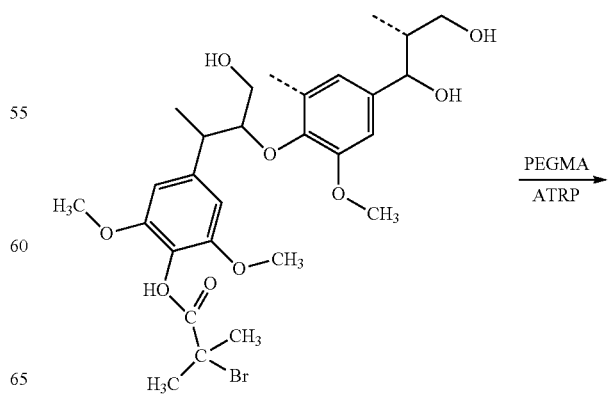

-continued

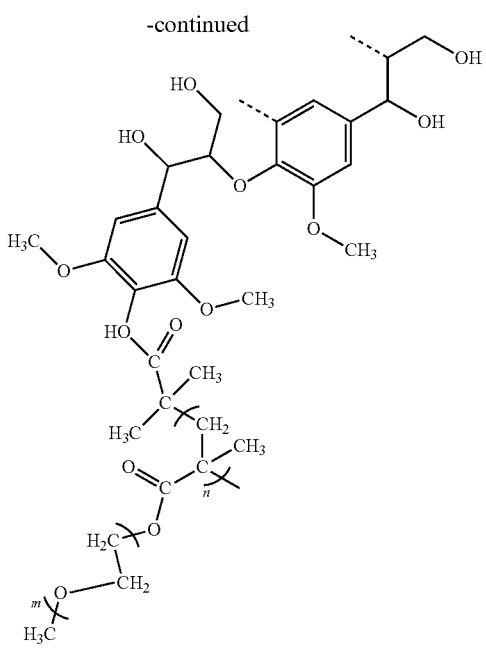

The copolymer may be a poly (alkylene oxide) alkyl ether (meth)acrylate-grafted oxygenated polyaromatic alcohol hyperbranched copolymer. The poly (alkylene oxide) alkyl ether (meth)acrylate forms the branch(es) of the copolymer.

The copolymer may be in the form of a hydrogel. Hence, exemplary, non-limiting embodiments of a hydrogel will now be disclosed. The hydrogel may comprise a copolymer having an oxygenated polyaromatic alcohol and a poly (alkylene oxide) alkyl ether (meth)acrylate.

The hydrogel may further comprise a cyclic oligosaccharide. The cyclic oligosaccharide may be a cyclodextrin or a derivative thereof such as α-cyclodextrin, β-cyclodextrin, γ-cyclodextrin or methyl-β-cyclodextrin. The cyclodextrin may be naturally synthesized by microorganisms or enzymes (such as cyclodextrin glycosyltransferase (CG-Tase)) or artificially synthesized.

The hydrogel may be formed by agitating a mixture of the copolymer with the cyclic oligosaccharide. The mixture may be a mixture of a copolymer aqueous solution and a cyclic oligosaccharide aqueous solution. Hence, the mixture may be an aqueous solution. Alternatively, the mixture may be made by dispersing or dissolving the cyclic oligosaccharide in powder form in a copolymer aqueous solution.

The copolymer aqueous solution that comprises about 0.1 wt % to about 80 wt %, about 0.1 wt % to about 10 wt %, about 0.1 wt % to about 20 wt %, about 0.1 wt % to about 30 wt %, about 0.1 wt % to about 40 wt %, about 0.1 wt % to about 50 wt %, about 0.1 wt % to about 60 wt %, about 0.1 wt % to about 70 wt %, about 10 wt % to about 80 wt %, about 20 wt % to about 80 wt %, about 30 wt % to about 80 wt %, about 40 wt % to about 80 wt %, about 50 wt % to about 80 wt %, about 60 wt % to about 80 wt %, about 70 wt % to about 80 wt %, about 1 wt % to about 80 wt % or about 1 wt % to about 40 wt % of the copolymer, based on the weight of the total solution (or mixture).

The mixture may contain about 1 wt % to about 50 wt %, about 1 wt % to about 5 wt %, about 1 wt % to about 10 wt %, about 1 wt % to about 20 wt %, about 1 wt % to about 30 wt %, about 1 wt % to about 40 wt %, about 5 wt % to about 50 wt %, about 10 wt % to about 50 wt %, about 20 wt % to about 50 wt %, about 30 wt % to about 50 wt %, about 40 wt % to about 50 wt %, or about 5 wt % to about 20 wt %, of the cyclic oligosaccharide, based on the weight of the total solution (or mixture).

In the hydrogel, the oxygenated polyaromatic alcohol, which is hydrophobic, forms a core which may aid in the self-assembly of the hydrogels. The oxygenated polyaromatic alcohol core may help the formation of inclusion complexes of the cyclic oligosaccharide with the poly (alkylene oxide) alkyl ether (meth)acrylate branches of the copolymer to aggregate into polypseudorotaxane microcrystals, forming physical crosslinks and inducing formation of a supramolecular polymer network. This consequently results in the gelation of the mixture to form the hydrogel.

The hydrogel may be injectable. The hydrogel may be biodegradable.

The hydrogel may be coloured, with the colour increasing in intensity by becoming more brown as the amount of oxygenated polyaromatic alcohol in the hydrogel increases. The colour of the hydrogel can include various shades of yellow or brown.

The hydrogel may have a storage modulus of about 0.01 Pa to about 100 GPa, depending on the test parameters (such as temperature, stain, frequency, etc). The storage modulus may be determined by test methods such as, but not limited to, rheometer, viscometry, etc. The mechanical property of the hydrogel may be tuned by changing the content of the poly (alkylene oxide) alkyl ether (meth)acrylate block (such as the chain length or molecular weight of the poly (alkylene oxide) alkyl ether (meth)acrylate or ratio of the poly (alkylene oxide) alkyl ether (meth)acrylate to the oxygenated polyaromatic alcohol) in the copolymer, adjusting the polymer concentration in the mixture or the concentration of the cyclic oligosaccharide in the mixture.

The hydrogel may be able to re-assemble into a gel from a liquid phase, that is, the hydrogel is able to self-heal. The self-healing capability may be possible over a range of temperatures, such as for example, at body temperature (of 37° C.). Hence, should the hydrogel structure be destroyed (example, by stress or under an application of a force) such that the gel phase turns into a semi-liquid or liquid gel composition, the gel composition is still able to self-heal to reconstitute into the hydrogel. The time taken for the hydrogel to self-heal may be a matter of seconds, or minutes, such as from 2 seconds to 5 minutes. It is to be noted that these time ranges are only provided as a guide and the actual time take may be more depending on the extent of damage and amount of the hydrogel. The ability of the hydrogel to self-heal may be due to the presence of the multiple branches of the poly (alkylene oxide) alkyl ether (meth)acrylate in the copolymer that may aid in enhancing the host-guest interaction and may accelerate the cross-linking of the supramolecular networks to reconstitute into the hydrogel.

The hydrogel may not be cytotoxic and may not cause any adverse toxicity effects on an organism when placed in vivo, or when in contact with a skin surface.

Exemplary, non-limiting embodiments of a method for forming a hydrogel will now be disclosed. The method comprise the step of adding a cyclic oligosaccharide to a copolymer to form a mixture that undergoes gelation to form the hydrogel, the copolymer comprising an oxygenated polyaromatic alcohol and a poly (alkylene oxide) alkyl ether (meth)acrylate.

Where the cyclic oligosaccharide is added as a powder into a solution of the copolymer, the method may comprise the step of agitating the mixture. The mixture may be agitated via mixing or sonication. The mixture may be a fluid or a solution at first, which then becomes progressively turbid dispersion upon agitation. The dispersion then forms the hydrogel.

Alternatively, where a solution of the cyclic oligosaccharide is mixed with a solution of the copolymer the mixture may not require agitation and may gradually form the hydrogel when left to stand.

Where the mixture is to be agitated, the mixture may be agitated at a temperature in a range of about 10° C. to about 50° C., about 10° C. to about 20° C., about 10° C. to about 30° C., about 10° C. to about 40° C., about 20° C. to about 50° C., about 30° C. to about 50° C., about 40° C. to about 50° C., about 20° C. to about 30° C., or about 30° C. to about 40° C. The temperature may be at ambient temperature, such as at room temperature (of about 25° C.) or at body temperature (of about 37° C.). Hence, the mixture may form the hydrogel across a range of temperatures, such as between about 10° C. to about 50° C., or about 25° C. to about 37° C.

Where the mixture is not to be agitated, the mixture can also form the hydrogel across a range of temperatures, such as between about 10° C. to about 50° C., or about 25° C. to about 37° C.

The time taken to form the hydrogel depends on the concentration and molecular weight of the polymers, and may range from 1 minute to up to 3 days. Where agitation is used, the time taken may be shortened.

The hydrogel may be used in biomedical and personal care industries.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIGS. 1A-1C comprise a series of $^1$H Nuclear Magnetic Resonance (NMR) spectra of lignin (Fig. A); lignin-Br (FIG. 1B); and lignin-PEGMA (FIG. 1C).

FIG. 2 shows the Fourier Transform Infrared Spectroscopy (FTIR) spectra of lignin, lignin-Br, Lig-PEG1, Lig-PEG2 and Lig-PEG3.

FIG. 3 shows a $^{13}$C NMR spectra of lignin-PEG1 in CDCl$_3$.

FIG. 4 shows the Differential Scanning calorimetry (DSC) curves of lignin, lignin-PEGMA-1g, lignin-PEGMA-2g and lignin-PEGMA-4g.

FIG. 5 shows the Thermogravimetric Analaysis (TGA) curves of lignin, Lig-PEG1, Lig-PEG2 and Lig-PEG4.

FIGS. 6A-6C comprises a series of photographs showing PEG-20% in sol state (FIG. 6A), Lig-PEG1-13% in gel state (FIG. 6B), hydrogel systems made from different polymers showing the varying colour shades of the hydrogel (FIG. 6C), where PEG refers to the control, LP4 refers to Lig-PEG4, LP2 refers to Lig-PEG2 and LP1 refers to Lig-PEG4.

FIG. 7 is a schematic diagram showing a proposed structure of the hydrogel based on PEGMA-grafted lignin and α-CD.

FIGS. 8A-8F comprise a series of graphs showing dynamic rheological behaviours, (A, C, E) storage (solid symbols) and loss (open symbols) moduli, (B, D, F) complex viscosity of lignin/α-CD hydrogels under amplitude sweep (oscillation strain from 0.01% to 100%). Fig. A and Fig. B show the rheological properties of Lig-PEG1 hydrogels with different concentrations of α-CD (6% to 14%), Fig. C and Fig. D show the rheological properties of the hydrogels with different concentrations of Lig-PEG1 (1% to 4%) while Fig. E and Fig. F show the hydrogel systems made with 2% different copolymers and 10% α-CD.

FIGS. 9A-9C comprise a series of tan delta graphs of lignin/α-CD hydrogels under amplitude sweep in which FIG. 9A shows lignin-PEG1 hydrogels with different concentration of α-CD (6% to 14%), FIG. 9B shows the hydrogels with different concentration of Lig-PEG1 (1% to 4%) and FIG. 9C shows the hydrogel systems made with 2% different copolymers and 10% α-CD.

FIGS. 10A-10C comprise a series of graphs showing the dynamic rheological behaviours of Lig-PEG2 hydrogels under amplitude sweep where FIG. 10A indicates the storage (solid symbols) and loss (open symbols) module, FIG. 10B indicates the tan delta values and FIG. 10C indicates the complex viscosity.

FIGS. 11A-11F comprise a series of graphs showing the dynamic rheological behaviours, FIGS. 11A and 11D show storage (solid symbols) and loss (open symbols) moduli; FIGS. 11B and 11E show Tan delta; FIGS. 11C and 11F show complex viscosity, of the Lig-PEG4/α-CD hydrogels under amplitude sweep (oscillation strain from 0.01% to 100%). FIGS. 11A-11C show the rheological properties of Lig-PEG4 hydrogels with different concentration of α-CD (6% to 14%), and FIGS. 11D to 11F show the rheological properties of the hydrogels with different concentration of Lig-PEG4 (1% to 4%).

FIGS. 12A-12C show a comparison of dynamic rheological behaviours (amplitude sweep), FIG. 12A shows storage (solid symbols) and loss (open symbols) moduli; FIG. 12B shows Tan delta; FIG. 12C shows complex viscosity, of the hydrogel systems made of different copolymers (4% copolymers with 10% α-CD).

FIGS. 13A-13C comprise a series of graphs showing the dynamic rheological behaviors, storage (solid symbols) and loss (open symbols) moduli; of the lignin/α-CD hydrogels under frequency sweep (oscillation frequency from 0.1 to 100 Hz). FIG. 13A shows Lig-PEG1 hydrogels with different concentration of α-CD (6% to 14%), FIG. 13B shows the hydrogels with different concentration of Lig-PEG1 (1% to 4%) and FIG. 13C shows the comparison of the hydrogel systems made of different copolymers.

FIGS. 14A-14C comprise a series of graphs showing the complex viscosities of the lignin/α-CD hydrogels under frequency sweep, where FIG. 14A refers to Lig-PEG1 hydrogels with different concentration of α-CD (6% to 14%), FIG. 14B refers to hydrogels with different concentration of Lig-PEG1 (1% to 4%), and FIG. 14C shows the comparison of the hydrogel systems made of different copolymers.

FIG. 15 shows the self-healing of LP1 2/10, LP2 2/10 and LP4 2/10 at 37° C. under a constant frequency of 1 Hz and repeat-shifted strains of 0.01% and 10%. The solid symbols represent storage modulus, and open symbols represent loss modulus. All the three hydrogels turned into sol under 10% strain and recovered to the solid state under 0.01% strain.

FIGS. 16A-16C comprise a series of graphs showing the cell viability (MTT assay) of lignin-PEGMA copolymers, α-CD and P(PEGMA) at 1 μM (FIG. 16A), 5 μM (FIG. 16B), and 10 μM (FIG. 16C), against human dermal fibroblasts for 24 hours, 48 hours and 72 hours.

EXAMPLES

Non-limiting examples of the invention will be further described in greater detail by reference to specific Examples, which should not be construed as in any way limiting the scope of the invention.

Example 1

Synthesis of Lignin ATRP Macroinitiators (Lignin-Br)

Kraft lignin (obtained from kraft pulping, Product No.: 370959, Mn=5000 g/mol, Mw=28 000 g/mol) was dried at 105° C. overnight before use. Then the dried lignin was cooled down to room temperature under nitrogen atmosphere. Lignin (Alkali, 3.0 g, 0.6 mmol, containing —OH 22.3 mmol) was weighted into a reaction flask. Subsequently, anhydrous N,N-dimethylacetamide (DMA, 30 ml, obtained from Sigma-Aldrich of St. Louis of Missouri of the United States of America) was injected into the reaction flask to dissolve the lignin under rapid stirring. Then triethylamine (TEA, 53.5 mmol, 7.46 ml, obtained from Sigma-Aldrich of St. Louis of Missouri of the United States of America) was added into the lignin solution. After that, 10 ml of anhydrous DMA containing 2-bromoisobutyryl bromide (BIBB, 44.6 mmol, 5.51 ml, obtained from Sigma-Aldrich of St. Louis of Missouri of the United States of America) was added dropwise into the lignin solution under rapid stirring during a period of 1 hour in ice-water bath. The reaction mixture was continued to stir for 1 day at room temperature.

Figure 1A:
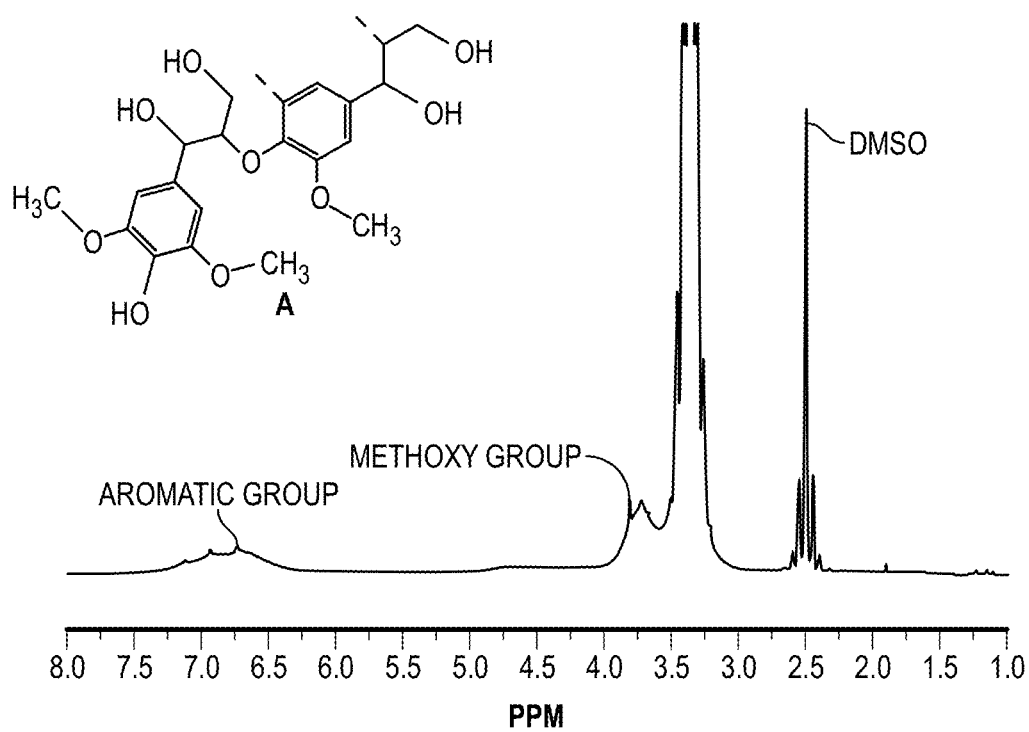
FIGS. 1A-1C
Figure 1B:
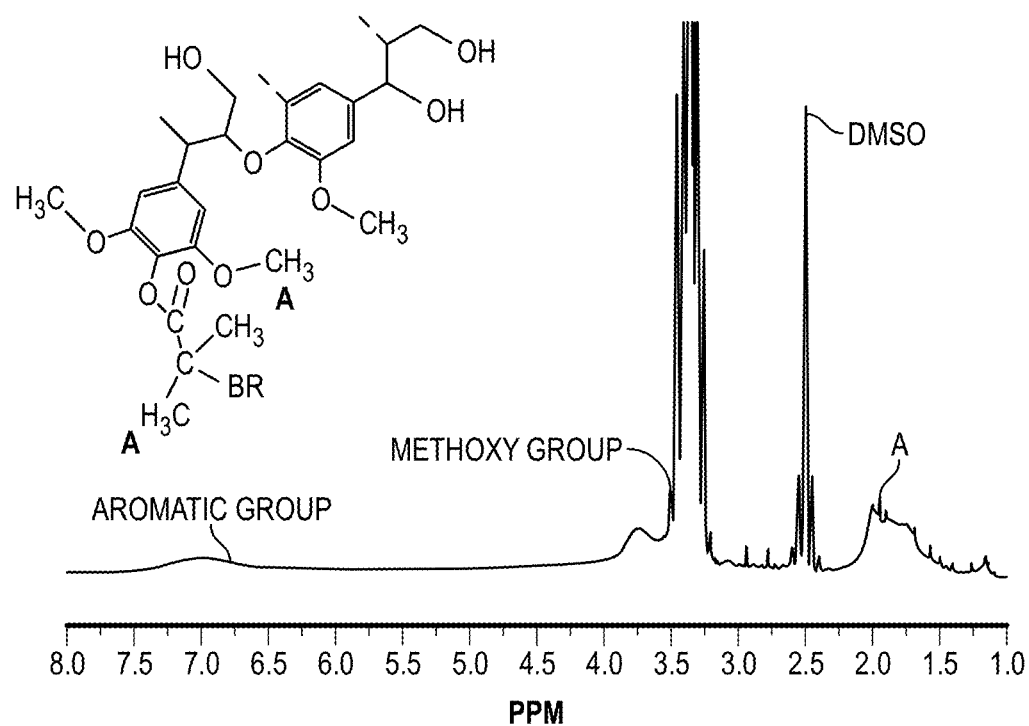

Following which, the reaction mixture was centrifuged and the supernatant was precipitated with 500 ml of ether. The tan gel-like precipitate was re-dissolved into tetrahydrofuran (THF, 50 ml, obtained from Sigma-Aldrich of St. Louis of Missouri of the United States of America) and the solution was then precipitated with 600 ml of ether. The brown powder of lignin macroinitiator was collected and dried under vacuum at 40° C. The number of initiator sites on lignin was determined by $^1$H NMR (NMR Bruker 400 MHz of the United States of America). Deuterated chloroform ($CDCl_3$) and deuterated dimethyl sulfoxide (DMSO-$d_6$, obtained from Sigma-Aldrich of St. Louis of Missouri of the United States of America) were used as a solvent to dissolve synthesized materials. Representative NMR data for unmodified lidninand lignin-Br are shown in FIG. 1A and FIG. 1B respectively. The natural polyhydroxyl aromatic lignin containing hydroxyl groups was readily modified by BIBB through esterification reaction. Compared to the 1H NMR spectra of unmodified lignin (FIG. 1A), FIG. 1B confirms the formation of 2-bromoisobutyryl ester on lignin, as there were characteristic chemical shifts at 1.4-2.2 ppm corresponding to the methyl protons of the initiating sites derived from both phenolic and aliphatic alcohols. FIG. 1B shows S (ppm) 1.4-2.2 (—$CH_3$ of initiation group), 3.5-4.3 (—$CH_3O$—), 6.0-8.0 (aromatic protons of lignin).

Figure 2:
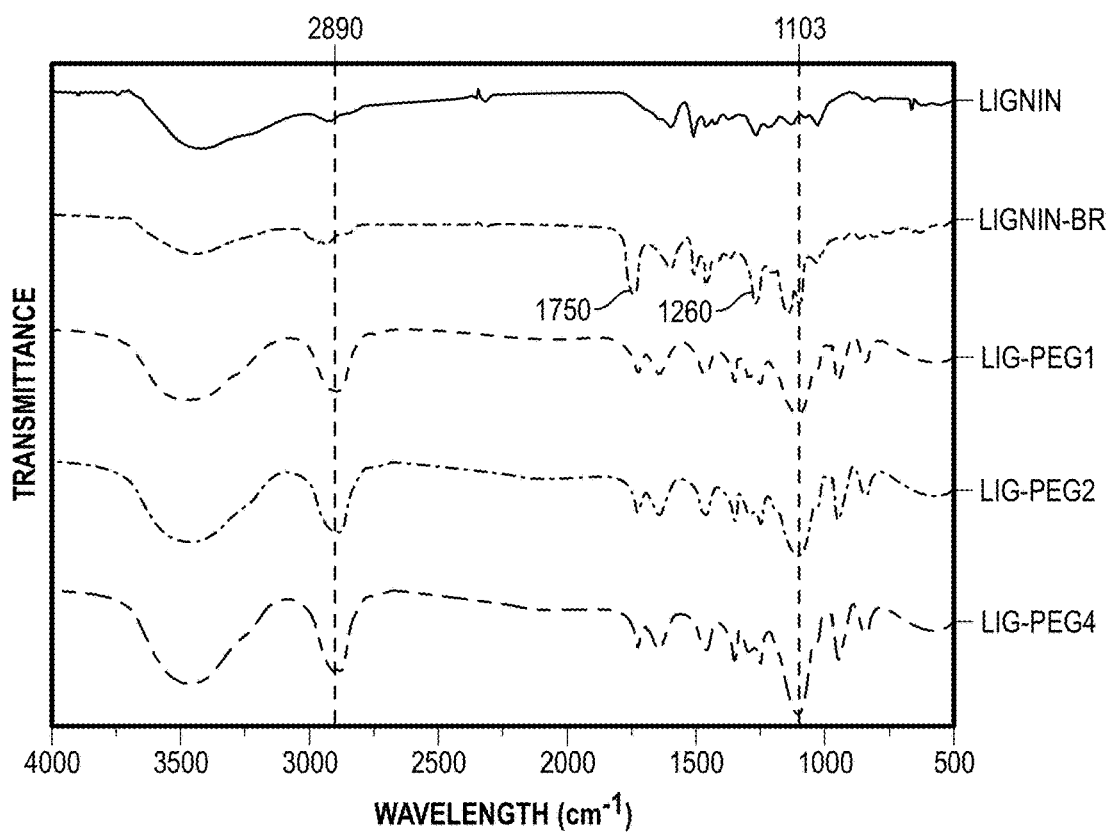
FIG. 2

As shown in FIG. 2, the FTIR-analysis of lignin-Br also showed the incorporation of the bromoisobutyryl ester moiety, as evident from the C=O and C—O stretching vibrations at 1750 and 1260 $cm^{-1}$, respectively. The concentration of initiator sites (bromoisobutyrate groups) on unit weight of lignin was calculated by adding the internal standard styrene in $^1$H NMR solution. The synthesized lignin macroinitiator had 2.3 mmol of initiator sites per gram of material. The lignin-Br was soluble in chloroform, THF and acetone, also indicating the successful modification of lignin.

Synthesis of Lignin-PEGMA Graft Copolymers

Poly(ethylene glycol) methyl ether methacrylate (PEGMA, average $M_n$ of 1100 g/mol, obtained from Sigma-Aldrich of St. Louis of Missouri of the United States of America) was purified by dissolving into anhydrous THF and passed through a column with inhibitor removed before use. The remaining THF was then removed by a rotary evaporator and vacuum-drying. An example of the synthesized lignin-PEGMA grafted copolymer can be the resultant product as shown in scheme 1 above. In scheme 1, the "n" value of the resultant lignin-PEGMA grafted copolymer can range from 1 to 10000 depending on the feed ratio while "m" is 23 in this instance.

PEGMA was grafted onto the lignin macroinitiator to form lignin-PEGMA copolymers via Atom-Transfer Radical-Polymerization (ATRP) reaction. Lignin-Br (MD=66%, 130 mg, 0.3 mmol Br), PEGMA (4 g, 3.6 mmol), 1,1,4,7,10,10-Hexamethyltriethylenetetramine (HMTETA, 83 mg, 0.36 mmol, obtained from Sigma-Aldrich of St. Louis of Missouri of the United States of America) and 10 ml of degassed acetone were added into a dry flask. The mixture was stirred at room temperature and purged with dry nitrogen for 20 minute. After that, CuBr (43 mg, 0.3 mmol, obtained from Sigma-Aldrich of St. Louis of Missouri of the United States of America) was added and the mixture was purged with dry nitrogen for another 10 minutes at room temperature. The mixture was continued to stir overnight at room temperature.

After that, the experiment was stopped by opening the flask and exposing the catalyst to air. The final tan mixture was diluted with THF and passed through a short neutral $Al_2O_3$ column with THF as eluent to remove copper catalyst. The resulting eluate solution was concentrated to 10 ml and precipitated with 1000 ml hexane. The brown product was collected by centrifugation, wasted with hexane and dried under vacuum at 40° C. As shown in Table 1, a series of lignin-PEGMA graft copolymers with different compositions of PEGMA were prepared under similar condition.

TABLE 1

| Polymers | Feed ratio | | $M_n$ (g/mol)$^a$ | $M_w$ (g/mol)$^a$ | poly-dispersity$^a$ | Mass % of lignin$^b$ |
| | Lignin-Br (g) | PEGMA (g) | | | | |
| --- | --- | --- | --- | --- | --- | --- |
| Lignin | 0.13 | | 5000 | 28,000 | 5.60 | |
| Lig-PEG1 | 0.13 | 1 | 38,706 | 48,011 | 1.24 | 12.9 |
| Lig-PEG2 | 0.13 | 2 | 49,074 | 59,190 | 1.2 | 10.2 |
| Lig-PEG4 | 0.13 | 4 | 64,992 | 71,623 | 1.23 | 7.7 |

$^a$Determined by GPC
$^b$Determined by GPC based on the molecule weight of lignin (5,000 g/mol).

Figure 1C:
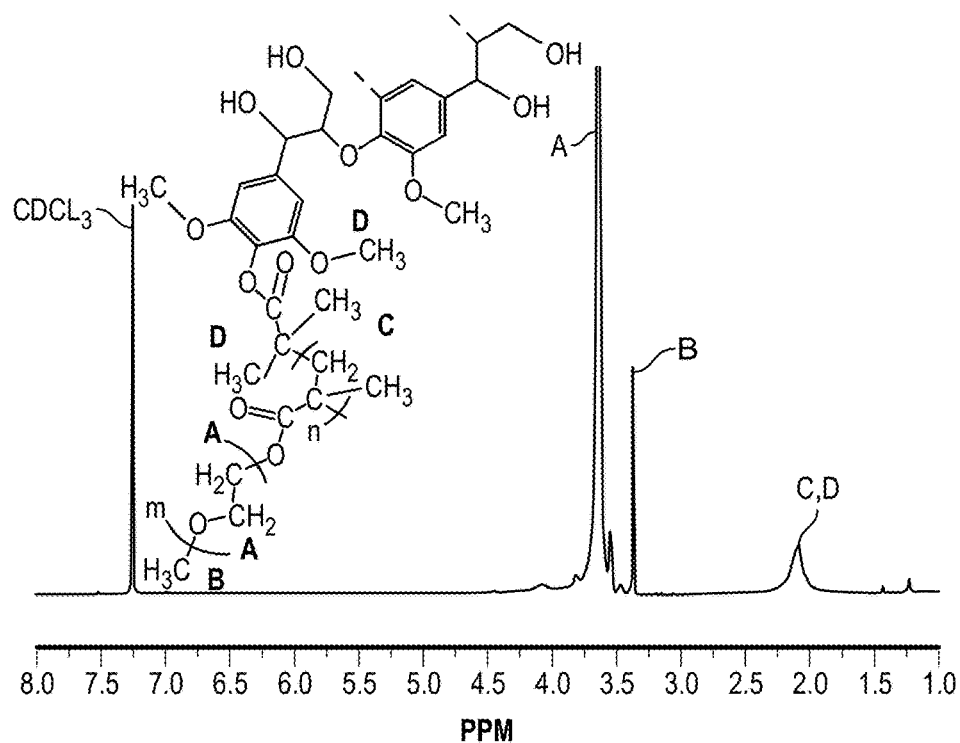

FIG. 1C shows the $^1$H NMR spectra of the lignin-PEGMA copolymer (Lig-PEG4 sample). FIG. 1C shows that characteristic peaks were present at 3.7 and 3.3 ppm that correspond to methylene and methyl protons from PEGMA. Due to lignin being present in a very small mass fraction, the lignin peaks for the grafted material were difficult to see.

Figure 3:
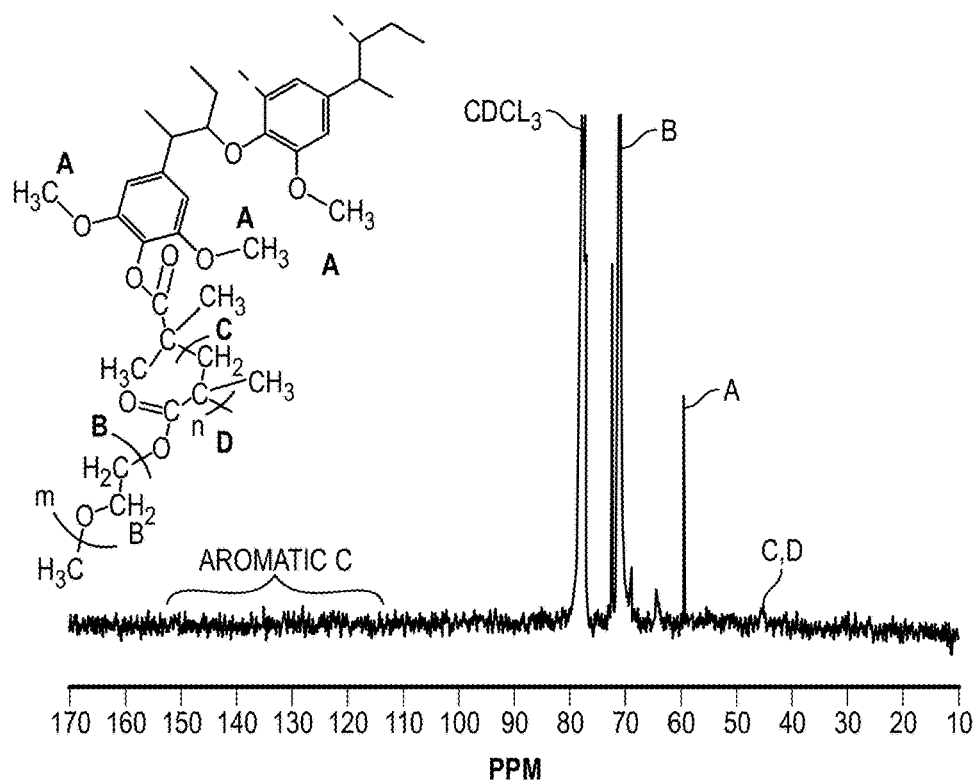
FIG. 3

The FTIR and $^{13}$C NMR data also showed the characteristic peaks of PEGMA in the spectra (FIG. 2 and FIG. 3 respectively). As seen in FIG. 2, the spectra of lignin-PEGMA copolymers showed characteristic bands of PEGMA, such as the bands appearing at 2890 cm$^{-1}$ assigned to the —CH group and 1103 cm$^{-1}$ assigned to the —C—O—C group. As seen in FIG. 3 (which was based on Lig-PEG1), the signals associated with the lignin aromatic ring and methoxyl groups were observed at 155~115 ppm and 58 ppm, respectively. The OCH$_2$ signal of PEGMA was seen at 70.3 ppm. Thus, FIG. 2 and FIG. 3 showed the successful grafting of PEGMA onto lignin.

In addition, molecular weight and polydispersity index of polymer samples were analyzed by Gel permeation chromatography (GPC, a Shimadzu SCL-10A and LC-8A system equipped with two Phenogel 5 μm 50 and 1000 Å columns in series and a Shimadzu RID-10A refractive index detector. THF was used as eluent at a flow rate of 0.30 mL/minute at 40° C. and monodispersed poly(ethylene glycol) standards were used to obtain a calibration curve). As shown in Table. 1, the unmodified lignin and PEGMA monomer had molecular weights of 5 and 1.1 kDa, respectively. The copolymers showed low polydispersities (about 1.2), and their molecular weights varied according to the feed ratio of lignin:PEGMA. The Mn of copolymers increased from 38.7 kDa for Lig-PEG1 to 65.0 kDa for Lig-PEG4. On the basis of the molecular weight of lignin, the contents of lignin in the copolymers were calculated and mass % of lignin were ranged from 7.7 for Lig-PEG4 to 12.9% for Lig-PEG1. Therefore, both the NMR and GPC results demonstrated the successful synthesis of the lignin-PEGMA copolymers.

The thermal properties of lignin and lignin-PEGMA copolymers were characterized by DSC and TGA. DSC thermal analysis was performed on a DSC (Q100, TA Instruments, USA) equipped with an autocool accessory and calibrated using indium. The following protocol was used for each sample: heating from room temperature to +180° C. at 20° C./min, holding at +180° C. from 5 minutes, cooling from +180 to −20° C. at 20° C./min, and finally reheating from −20 to +180° C. at 20° C./min. Data were collected during the second heating run. TGA was carried out on a thermogravimetric analyzer (Q500, TA Instruments, USA). Samples were heated at 20° C./min from room temperature to 700° C. in a dynamic nitrogen atmosphere (flow rate=60 mL/min). The thermal properties are shown in Table 2.

TABLE 2

| Polymers | $T_m$ (° C.)$^a$ | Enthalpy (J/g) | $T_d$ (° C.)$^a$ | $T_p$ (° C.)$^a$ | Weight % remained at 500° C. | Mass % of lignin$^b$ |
|---|---|---|---|---|---|---|
| Lignin | N.A. | N.A. | 260 | 349 | 58.0 | 100 |
| Lig-PEG1 | 33.08 | 87.99 | 352 | 415 | 8.2 | 14.1 |
| Lig-PEG2 | 34.54 | 94.39 | 360 | 416 | 4.8 | 8.2 |
| Lig-PEG4 | 34.79 | 102.9 | 355 | 412 | 3.4 | 5.8 |

$^a$$T_m$ is melt temperature determined by DSC. $T_d$ is thermal decomposition temperature, defined as the temperature at which the mass of the sample is 5% less than its mass measured at 50° C. $T_p$ is the derivative peak temperature.
$^b$Determined by TGA based on weight % remaining at 500° C.

Figure 4:
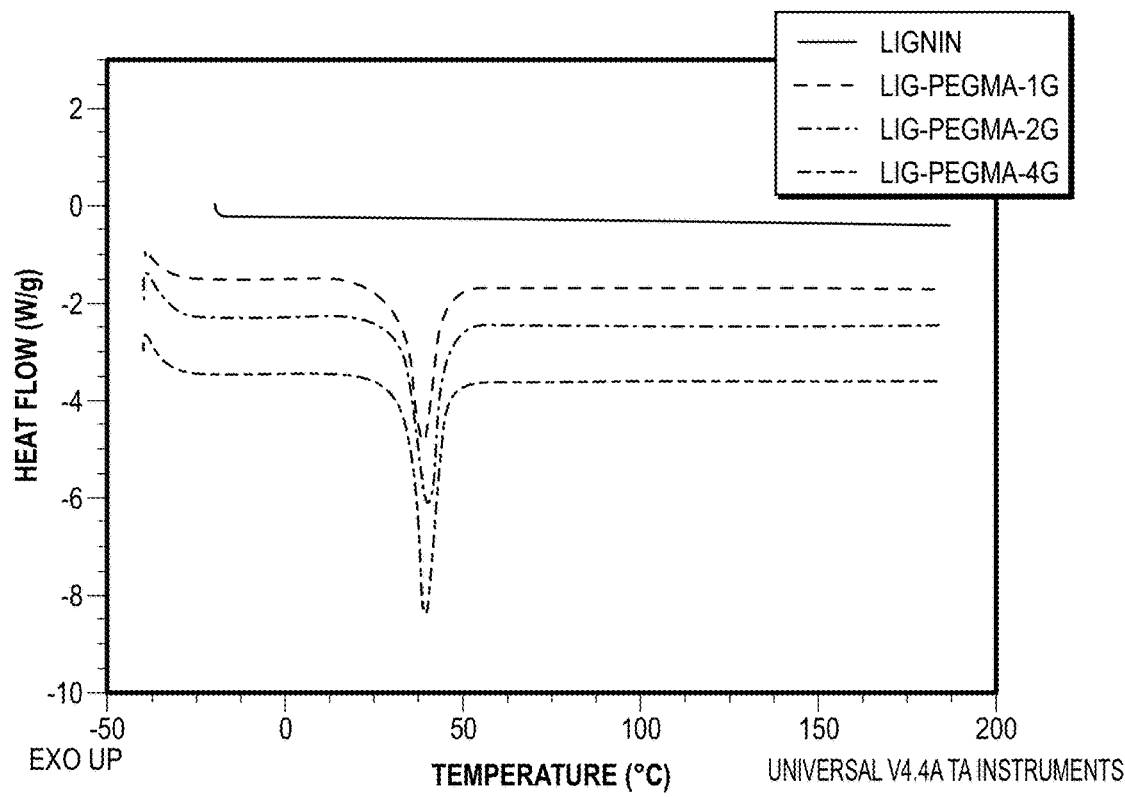
FIG. 4
Figure 5:
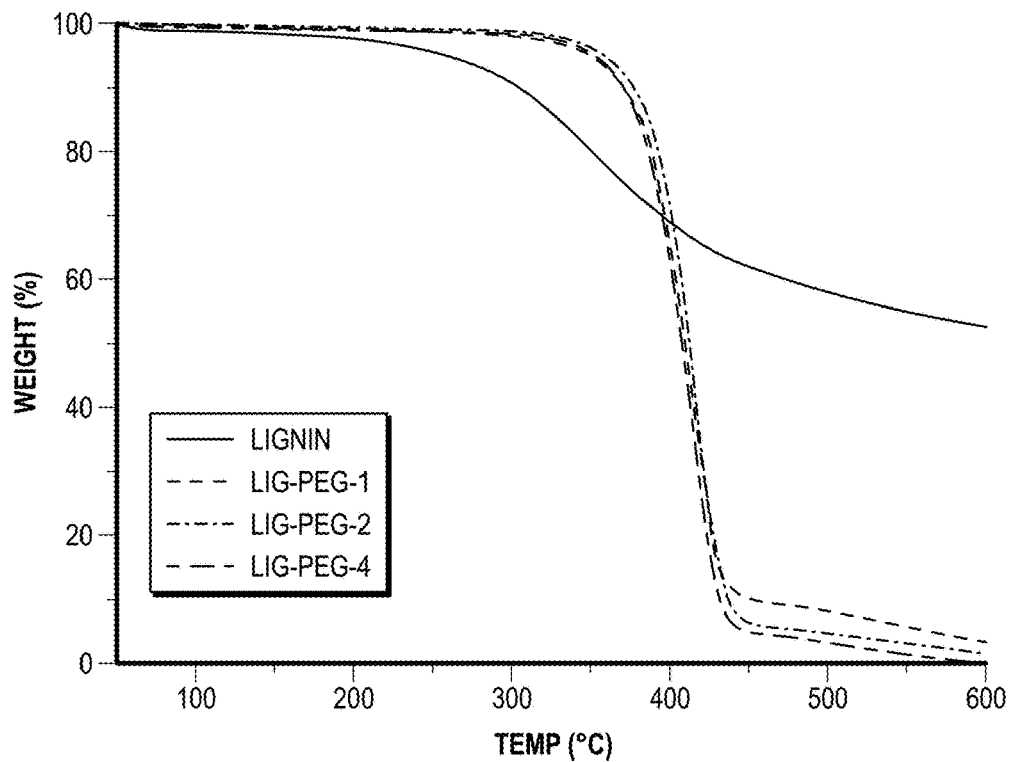
FIG. 5

Unmodified lignin did not have a melting temperature ($T_m$) or enthalpy, whereas the lignin-PEGMA copolymers exhibited their $T_m$ at about 34° C. resulting from the melting of the PEGMA chains (see FIG. 4). The melting peaks became larger and clearer with the increasing PEGMA contents, while their enthalpies increased from 88 g/mol for Lig-PEG1 to 103 g/mol for Lig-PEG4 with increasing contents of PEGMA. The thermal stabilities of lignin and lignin-PEGMA copolymers were investigated by TGA under N$_2$ atmosphere (see Table 2 and FIG. 5). The unmodified lignin thermally decomposed slowly and showed 5% of the weight loss (thermal decomposition temperature, $T_d$) at 260° C. Lignin's aromatic chemical structure gave a very high char yield (around 40 wt % at 500° C.). Compared to lignin, the lignin-PEGMA copolymers showed higher $T_d$ values (above 350° C. for 5% of the weight loss), and their derivative peak temperatures ($T_p$) increased to about 415° C. Lig-PEG1, Lig-PEG2 and Lig-PEG4 remained 8.2, 4.8 and 3.4% of their original weights. As PEG segments were completely degraded at 500° C., the residuals of the lignin-PEGMA copolymers were the remaining lignin. After calculation, the mass % of lignin in the copolymers ranged from 5.8% for Lig-PEG4 to 14.1% for Lig-PEG1, in agreement with the results calculated by GPC. Overall, the grafting of PEGMA onto lignin increased lignin's thermal stability, but the length of PEGMA chain did not significantly influence the thermal stabilities of the copolymers.

Example 2

Hydrogel Formation Between Lignin-PEGMA Copolymers and α-CD

A weighted amount of lignin-PEGMA copolymer was added to phosphate buffered saline (PBS) under sonication. After the solutions were mixed well, α-CD (in PBS) were weighted out and added into the lignin-PEGMA solution under stirring and sonication. The detailed composition and appearance of each hydrogel is given in Table 3.

Figure 6A:
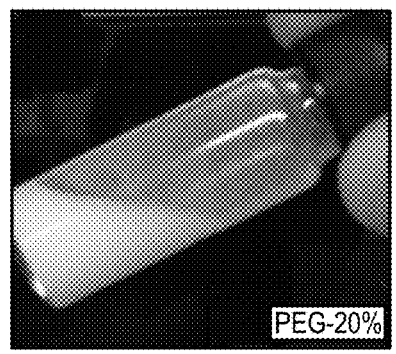
FIGS. 6A-6C
Figure 6B:
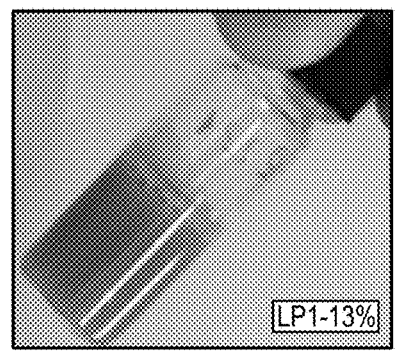
Figure 7:
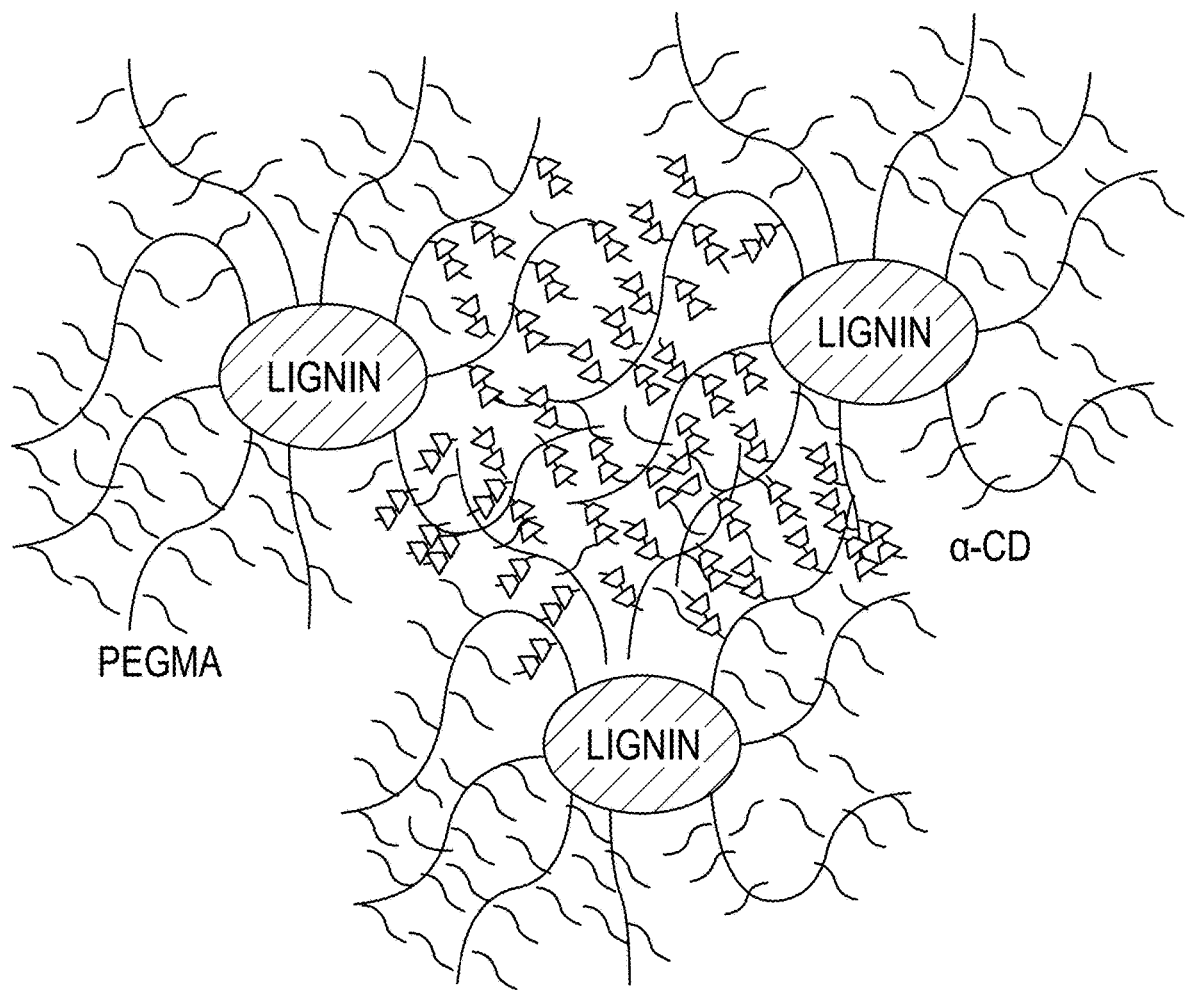
FIG. 7

As shown in Table 3, in this example only, the systems containing 0.5 wt % (and below) of copolymers or 5 wt % (and below) of α-CD in PBS did not form hydrogels in both room temperature (25° C.) and body temperature (37° C.). It is theorized that even if the concentrations are below the above values, if the molecular weight of the copolymer is high enough, a hydrogel can still be formed. The increase in the polymer concentration led to the gel formation within 2 minutes and it was found that the mixture of 1% (and above) of the copolymer solution with 6% (and above) of α-CD solution rendered hydrogels (FIG. 6B). It was reported that linear PEG took a long time (several hours) to form hydrogels, and the gelation time highly depended on the molecular weight of PEG chains, polymer structure and concentration. Here, the hyperbranched lignin-based copolymers of the present disclosure were able to remarkably reduce the gelation time even at a very low polymer concentration. Only 1% of such copolymer was enough for gel formation, whereas the P(PEGMA)/α-CD (as the control) was not able to form any gel even at 10% polymer concentration; the control only formed a flowable inclusion complex emulsion. Compared to a linear PEGMA structure of the control, the unique complex three-dimensional network structure of lignin-PEGMA copolymers presented a hydrophobic lignin core which aids in the self-assembly of the hydrogels. The lignin core helped the inclusion complexes formation by α-CD with PEGMA branches of the copolymers to aggregate into polypseudorotaxane microcrystals, crosslinking physically and inducing formation of a supramolecular polymer network (FIG. 7), consequently resulting in the gelation of the solution. Unlike the reported linear PEG/α-CD hydrogels, the polypseudorotaxane formation and the association of the threaded α-CD in the lignin hydrogels of the present disclosure almost occurred synchronously, leading to the rapid self-assembly of a three-dimensional network.

TABLE 3

| Formulation code | Polymer used | Gel composition | | Appearance of lignin/α-CD | |
|---|---|---|---|---|---|
| | | Copolymer (w/v %) | α-CD (w/v %) | 25° C. | 37° C. |
| PEG 10/10 | P(PEGMA) | 10 | 10 | Sol | Sol |
| LP1 0.5/10 | Lig-PEG1 | 0.5 | 10 | Sol | Sol |
| LP1 1/5 | Lig-PEG1 | 1 | 5 | Sol | Sol |
| LP1 1/6 | Lig-PEG1 | 1 | 6 | Gel | Gel |
| LP1 1/10 | Lig-PEG1 | 1 | 10 | Gel | Gel |
| LP1 2/6 | Lig-PEG1 | 2 | 6 | Gel | Gel |
| LP1 2/8 | Lig-PEG1 | 2 | 8 | Gel | Gel |
| LP1 2/10 | Lig-PEG1 | 2 | 10 | Gel | Gel |
| LP1 2/12 | Lig-PEG1 | 2 | 12 | Gel | Gel |
| LP1 2/14 | Lig-PEG1 | 2 | 14 | Gel | Gel |
| LP1 3/10 | Lig-PEG1 | 3 | 10 | Gel | Gel |
| LP1 4/10 | Lig-PEG1 | 4 | 10 | Gel | Gel |
| LP2 0.5/10 | Lig-PEG2 | 0.5 | 10 | Sol | Sol |
| LP2 1/5 | Lig-PEG2 | 1 | 5 | Sol | Sol |
| LP2 1/6 | Lig-PEG2 | 1 | 6 | Gel | Gel |
| LP2 1/10 | Lig-PEG2 | 1 | 10 | Gel | Gel |
| LP2 2/6 | Lig-PEG2 | 2 | 6 | Gel | Gel |
| LP2 2/8 | Lig-PEG2 | 2 | 8 | Gel | Gel |
| LP2 2/10 | Lig-PEG2 | 2 | 10 | Gel | Gel |
| LP2 2/12 | Lig-PEG2 | 2 | 12 | Gel | Gel |
| LP2 2/14 | Lig-PEG2 | 2 | 14 | Gel | Gel |
| LP2 3/10 | Lig-PEG2 | 3 | 10 | Gel | Gel |
| LP2 4/10 | Lig-PEG2 | 4 | 10 | Gel | Gel |
| LP4 0.5/10 | Lig-PEG4 | 0.5 | 10 | Sol | Sol |
| LP4 1/5 | Lig-PEG4 | 1 | 5 | Sol | Sol |
| LP4 1/6 | Lig-PEG4 | 1 | 6 | Gel | Gel |
| LP4 1/10 | Lig-PEG4 | 1 | 10 | Gel | Gel |
| LP4 2/6 | Lig-PEG4 | 2 | 6 | Gel | Gel |
| LP4 2/8 | Lig-PEG4 | 2 | 8 | Gel | Gel |
| LP4 2/10 | Lig-PEG4 | 2 | 10 | Gel | Gel |
| LP4 2/12 | Lig-PEG4 | 2 | 12 | Gel | Gel |
| LP4 2/14 | Lig-PEG4 | 2 | 14 | Gel | Gel |
| LP4 3/10 | Lig-PEG4 | 3 | 10 | Gel | Gel |
| LP4 4/10 | Lig-PEG4 | 4 | 10 | Gel | Gel |

Figure 6C:
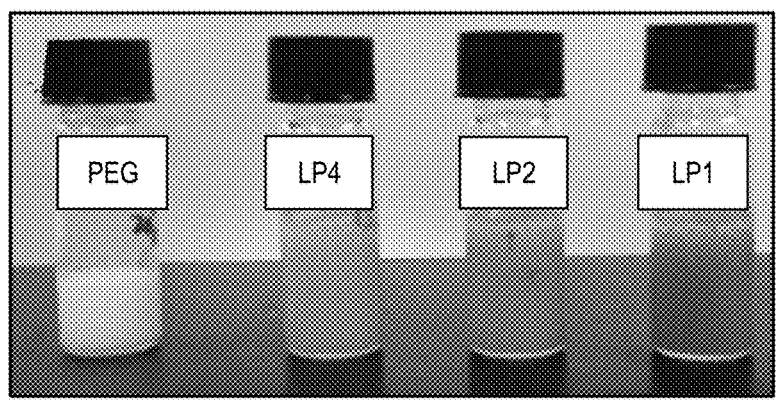

In addition, FIG. 6C shows that lignin-based hydrogels exhibited various colour tones due to the different contents of lignin in the copolymers (the highest content of lignin led to the brownest colour of the hydrogel).

Example 3

Rheological Studies of Lignin/α-CD Hydrogels

To investigate the effects of the amounts of α-CD, lignin-PEGMA copolymer and their molecular weights on the viscoelastic properties of the supramolecular hydrogels, amplitude sweep measurements were carried out by a Discovery Hybrid Rheometer 3 (TA Instrument, of the United States of America) fitted with 20 mm parallel-plate geometry at 37° C. The test methods employed were oscillatory amplitude sweeps at a constant frequency of 1 Hz. The storage (G') and the loss (G") moduli were recorded while the strain increased from 0.01% to 100%. A frequency sweep test was also conducted on each sample to determine their viscoelastic behaviours at a constant oscillation stain of 0.1% and over a frequency range of 0.1 to 100 Hz.

Figure 8A:
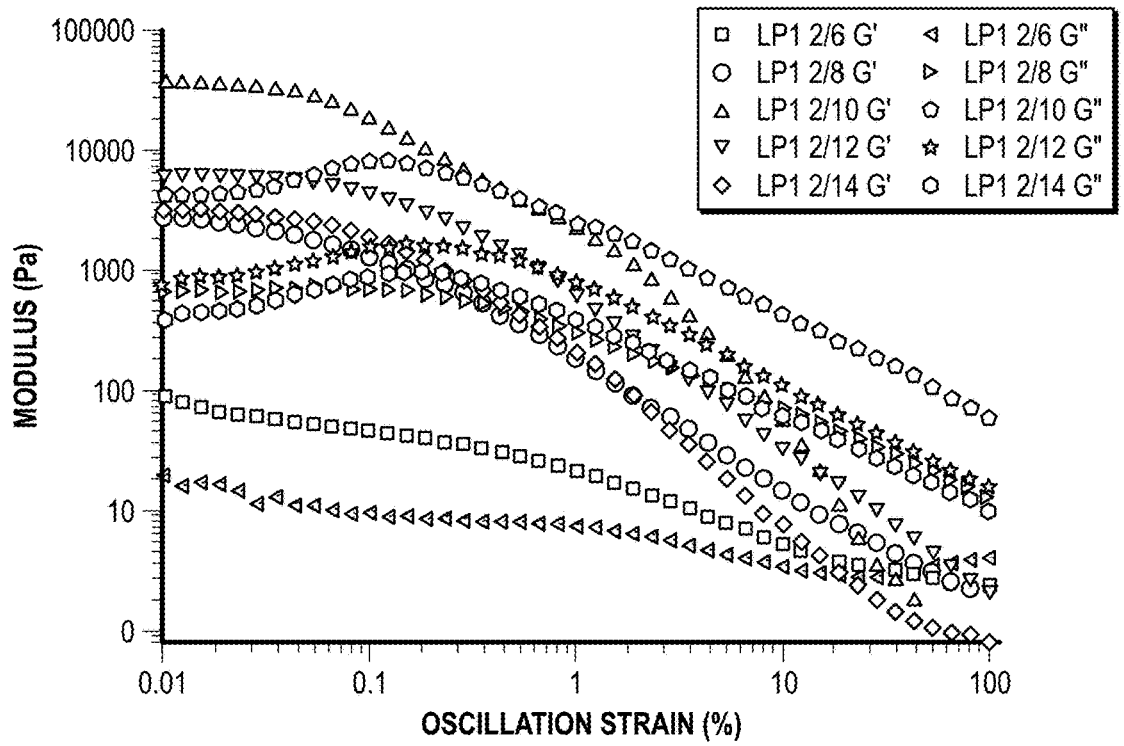
FIGS. 8A-8F
Figure 8B:
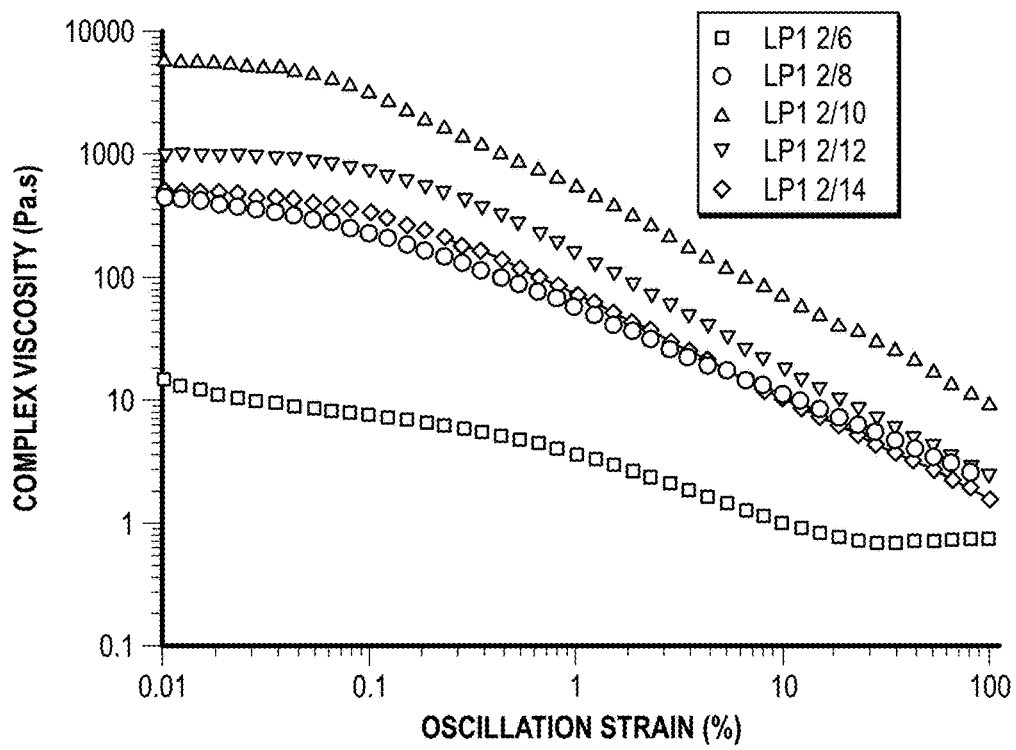
Figure 8C:
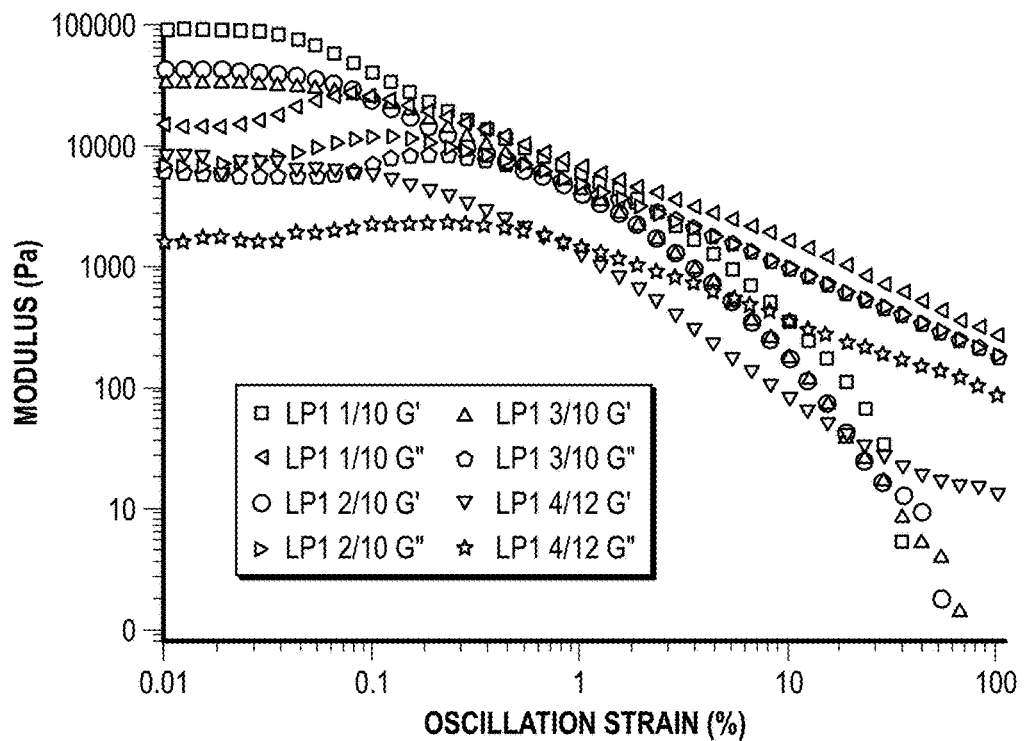
Figure 8D:
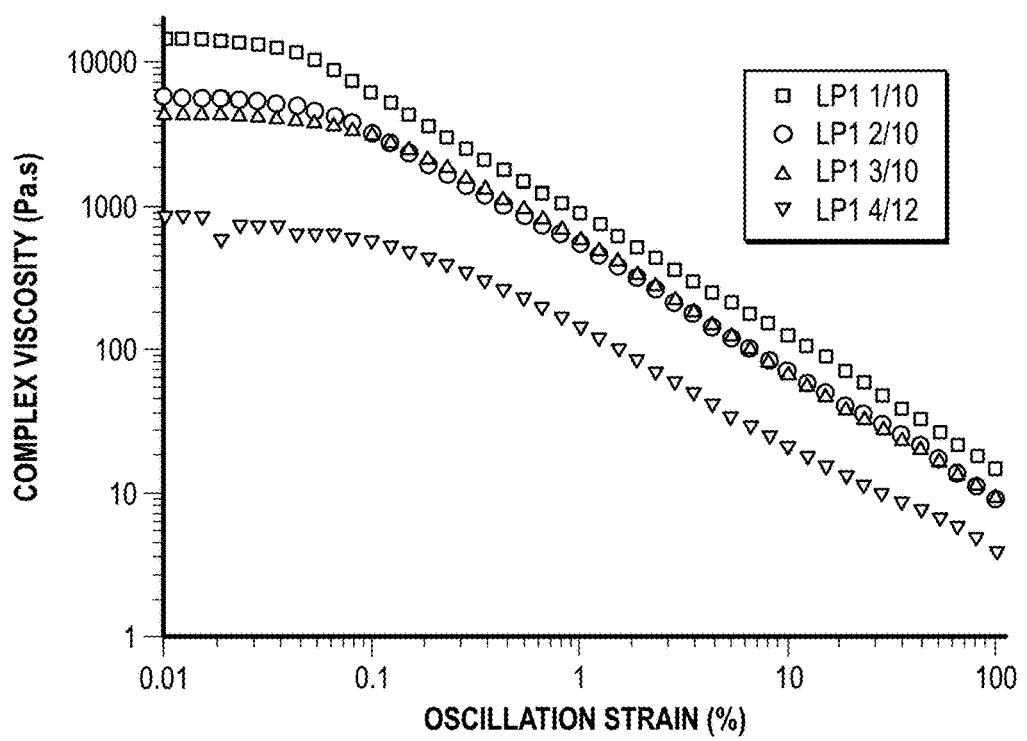
Figure 8E:
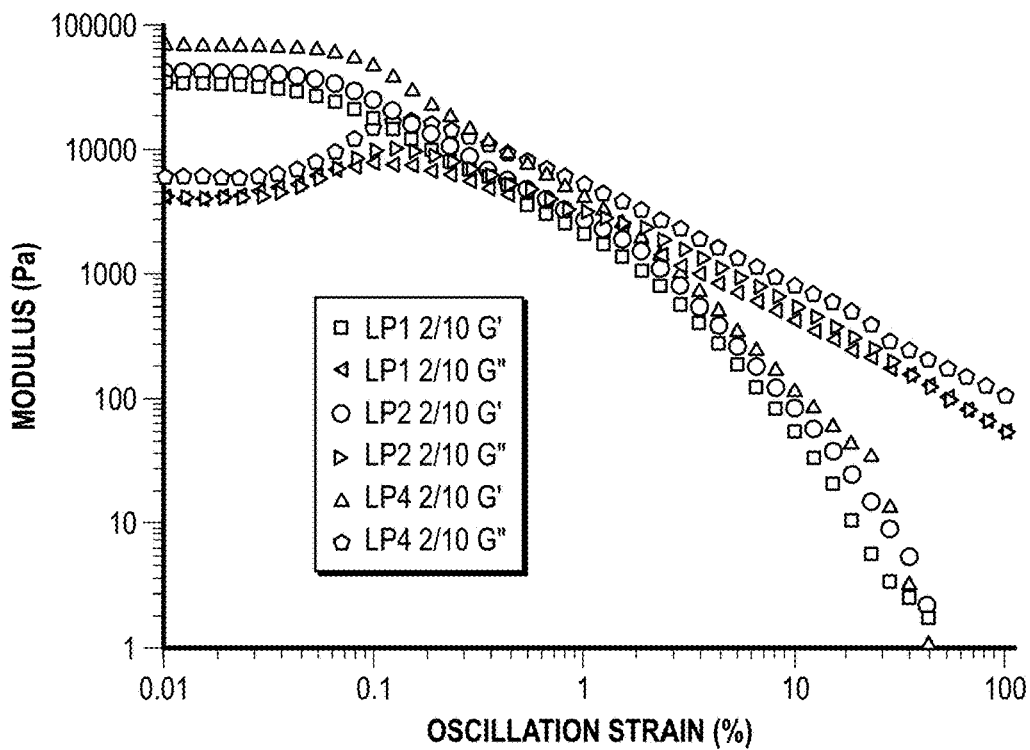
Figure 8F:
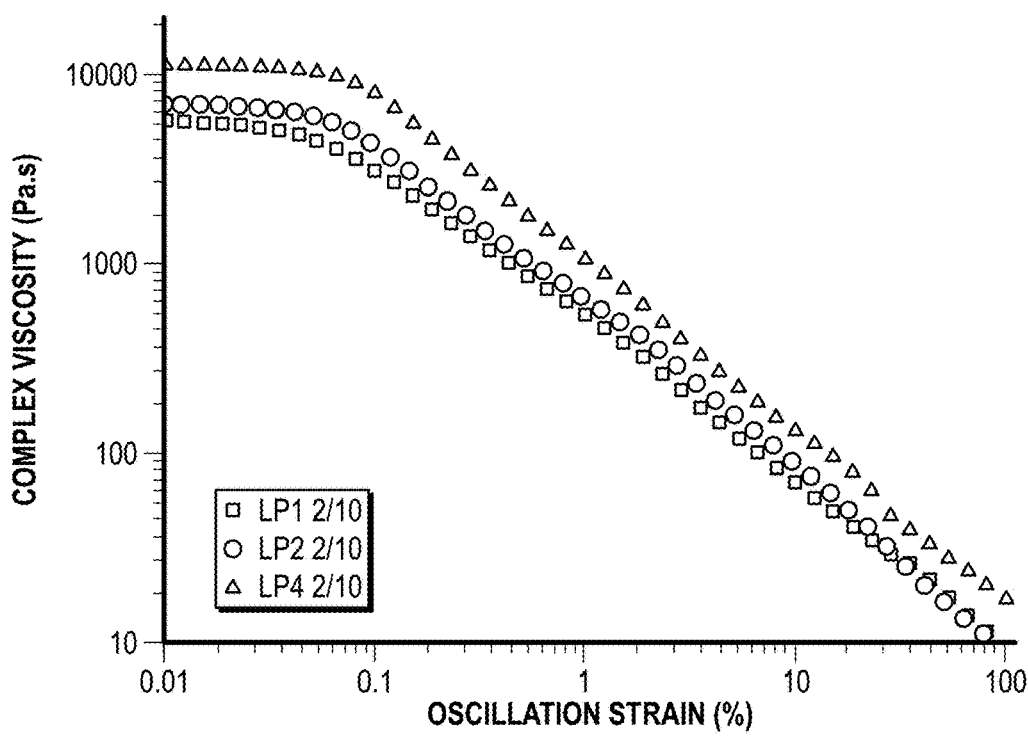
Figure 9A:
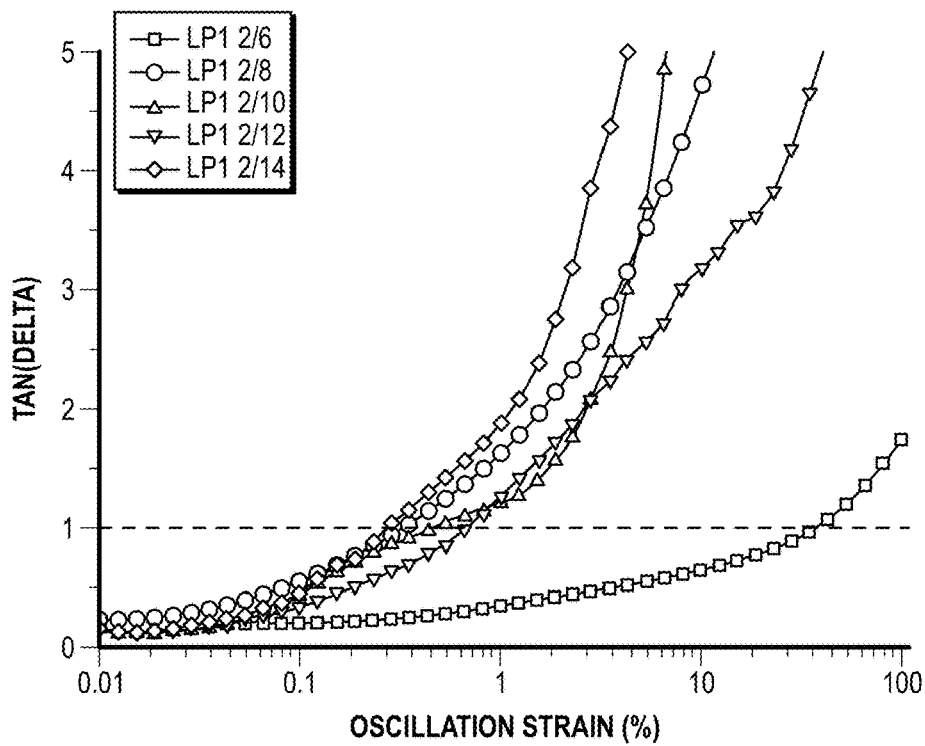
FIGS. 9A-9C
Figure 9B:
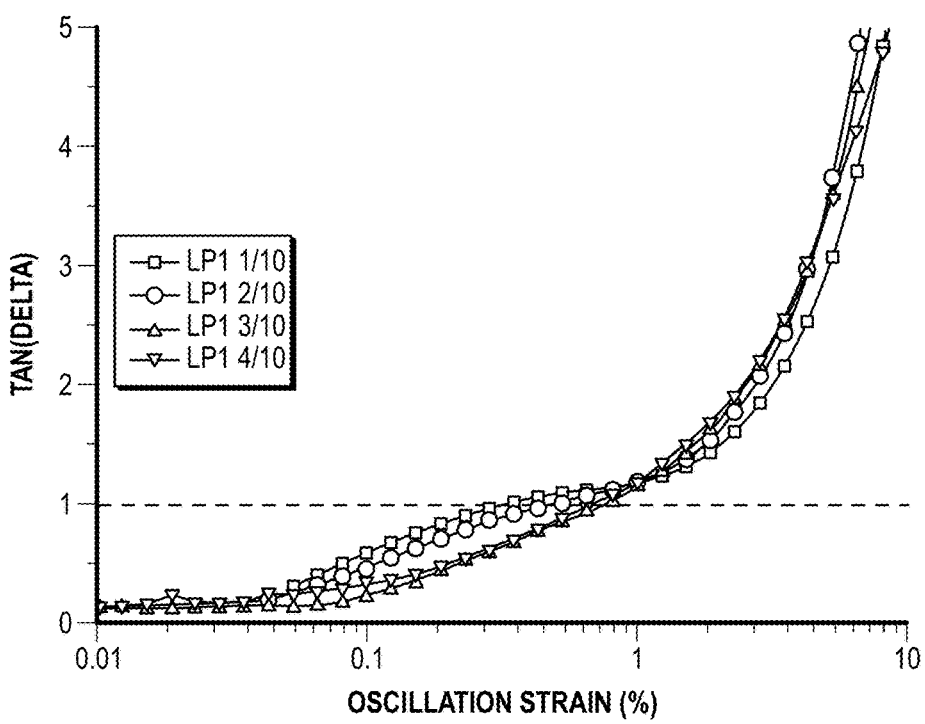
Figure 9C:
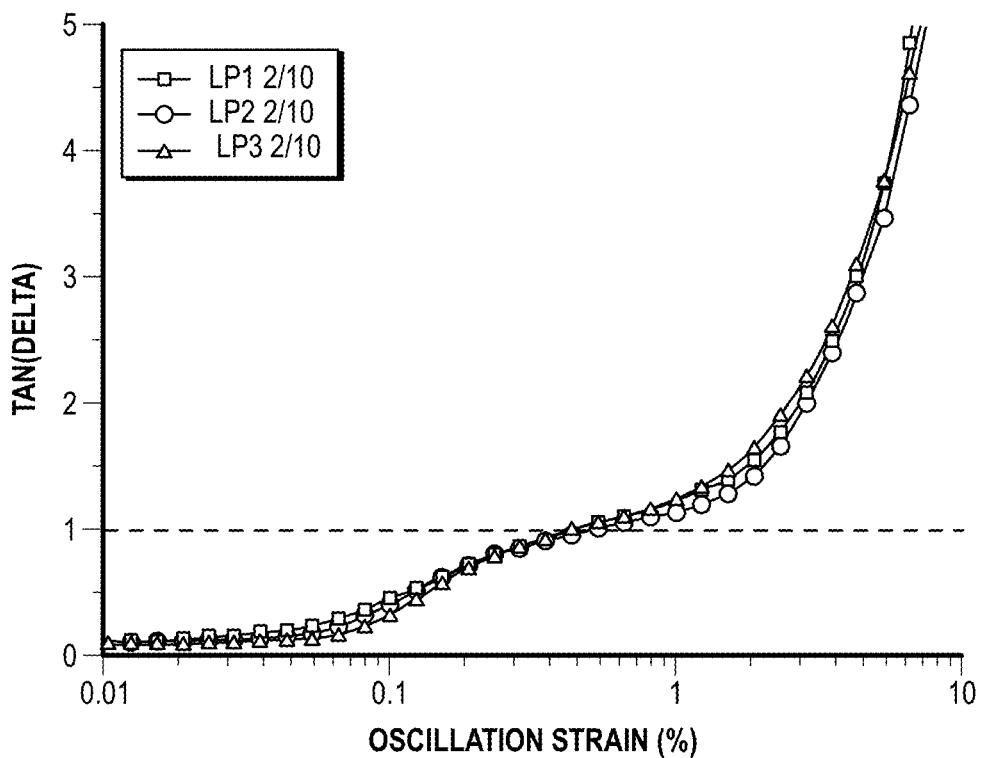

FIGS. 8A-8F show the viscoelastic behavior (storage and loss moduli, complex viscosity) of lignin/α-CD hydrogels as a function of oscillation stain. Results indicated that the lignin hydrogels were mechanically responsive systems and their rheological properties varied according to the change of stress or stain. At a low oscillation stain (<0.1%), storage modulus (G') and loss modulus (G") were constant, indicating that the gel structures were intact and undisturbed. This region is known as the linear-viscoelastic (LVE) region (G'>G" or tan δ=G"/G'<1), in which the materials are highly structured and have solid-like behavior. As oscillation stain increased, G' and complex viscosity started to decrease, whereas tan δ began to increase (see FIGS. 9A-9C, which show the tan delta of lignin/αCD hydrogels under amplitude sweep. FIG. 9A shows Lig-PEG1 hydrogels with different concentration of α-CD (6% to 14%), FIG. 9B presents the hydrogels with different concentration of Lig-PEG1 (1% to 4%), and FIG. 9C shows the hydrogel systems made with 2% different copolymers and 10% α-CD). The materials became progressively more fluid-like and eventually G" exceeded G' whereas tan δ values were beyond 1 with the increasing oscillation stain. The intersection point of G' and G" (G'=G" or tan δ=1) represented a transition of the hydrogel from solid-like (Gel) to liquid-like (Sol) behavior. The high Tan δ (G'<G") suggested that a high stress or stain could destroy the cross-linked polypseudorotaxanes and crystalline structure in the hydrogels, resulting in largely unassociated inclusion complexes in the aqueous system.

Figure 10A:
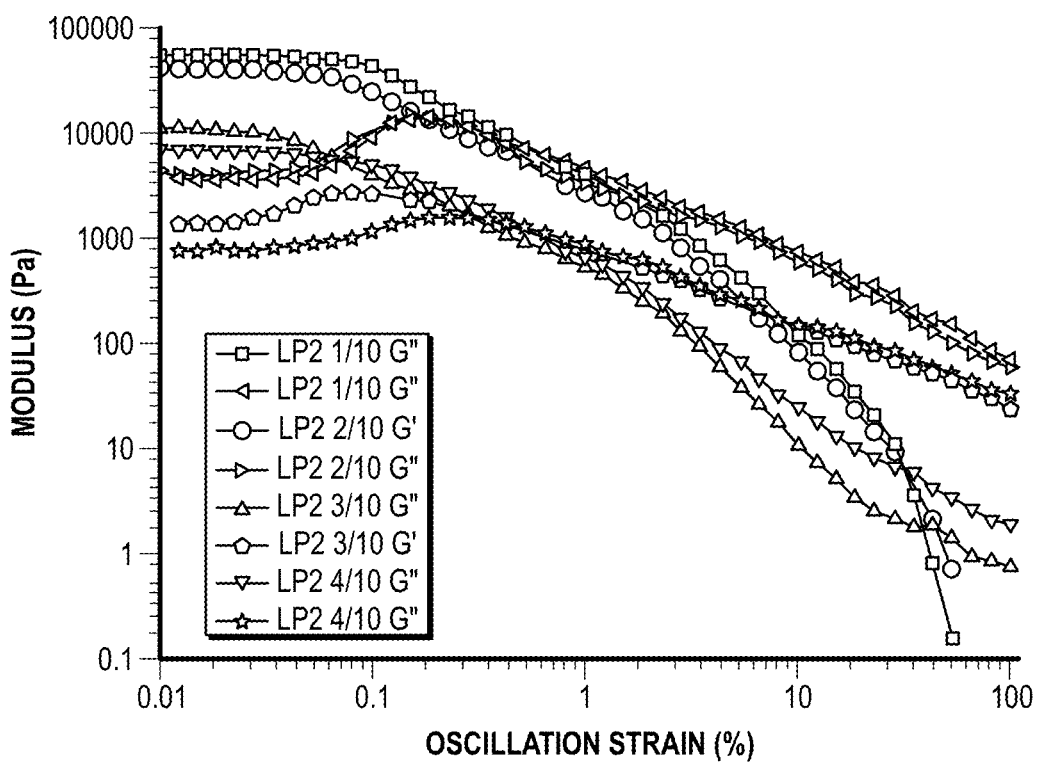
FIGS. 10A-10C
Figure 10B:
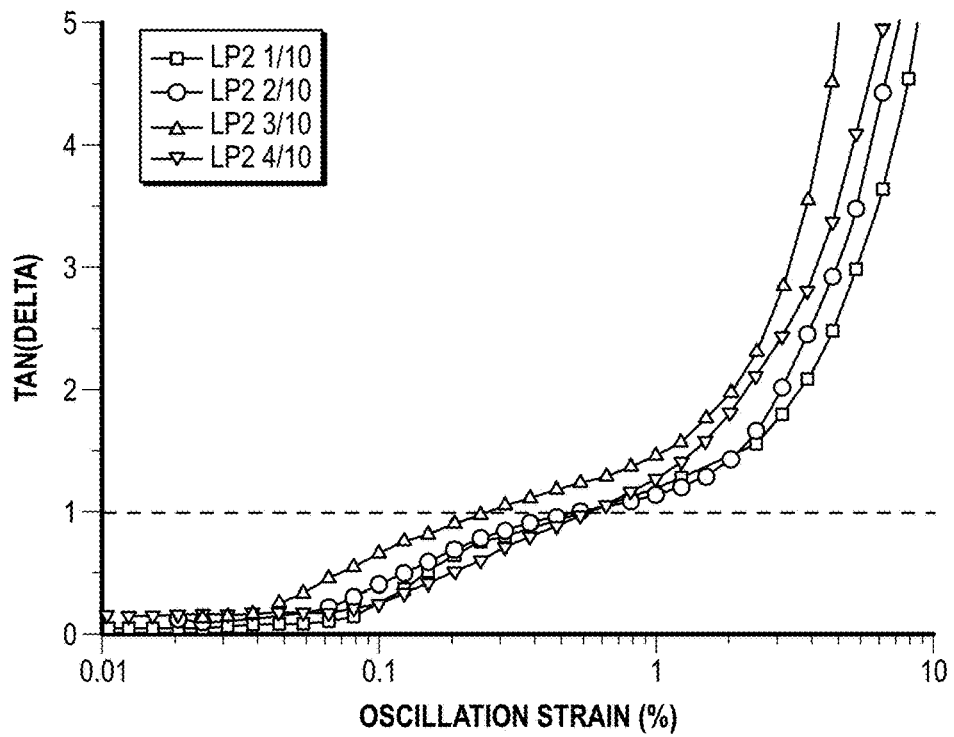
Figure 10C:
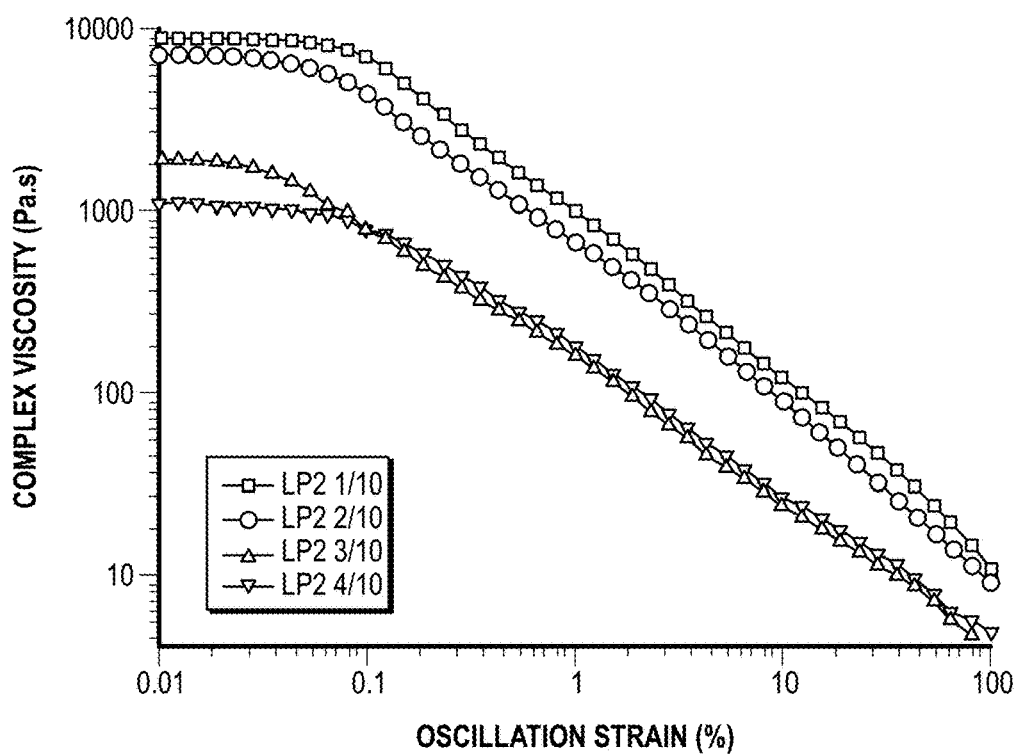
Figure 11A:
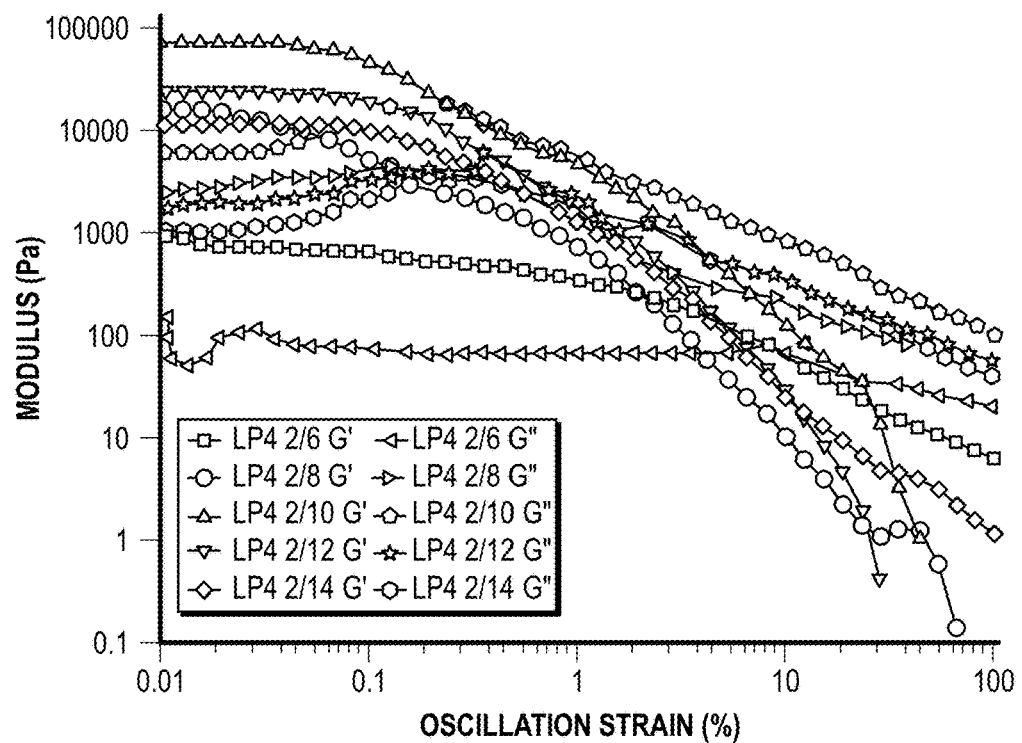
FIGS. 11A-11F
Figure 11B:
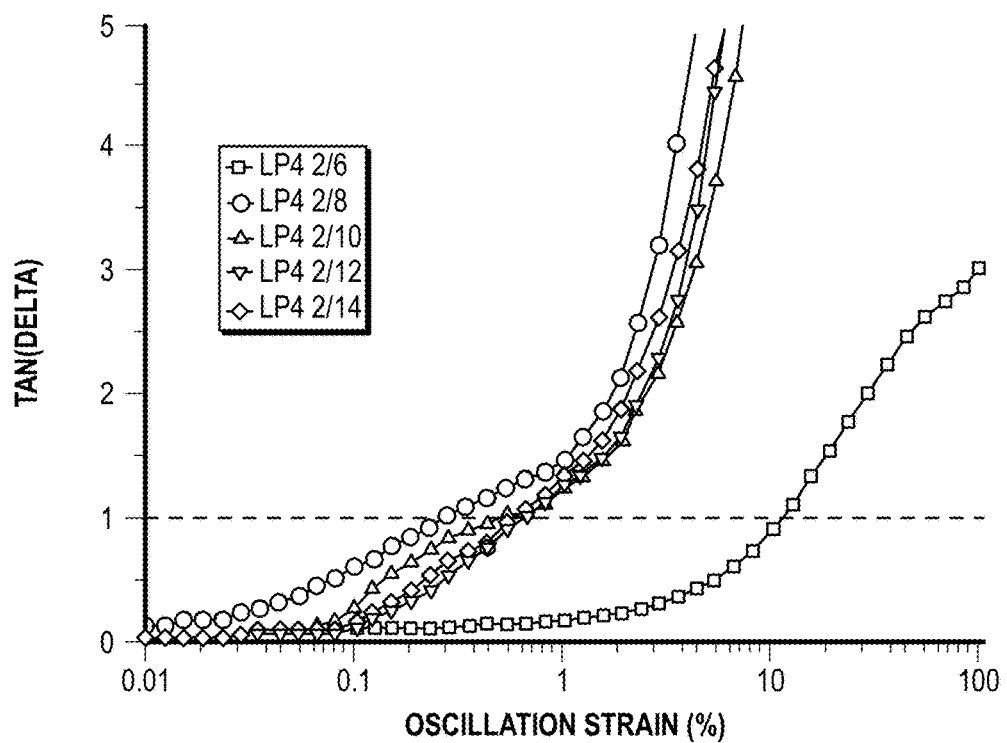
Figure 11C:
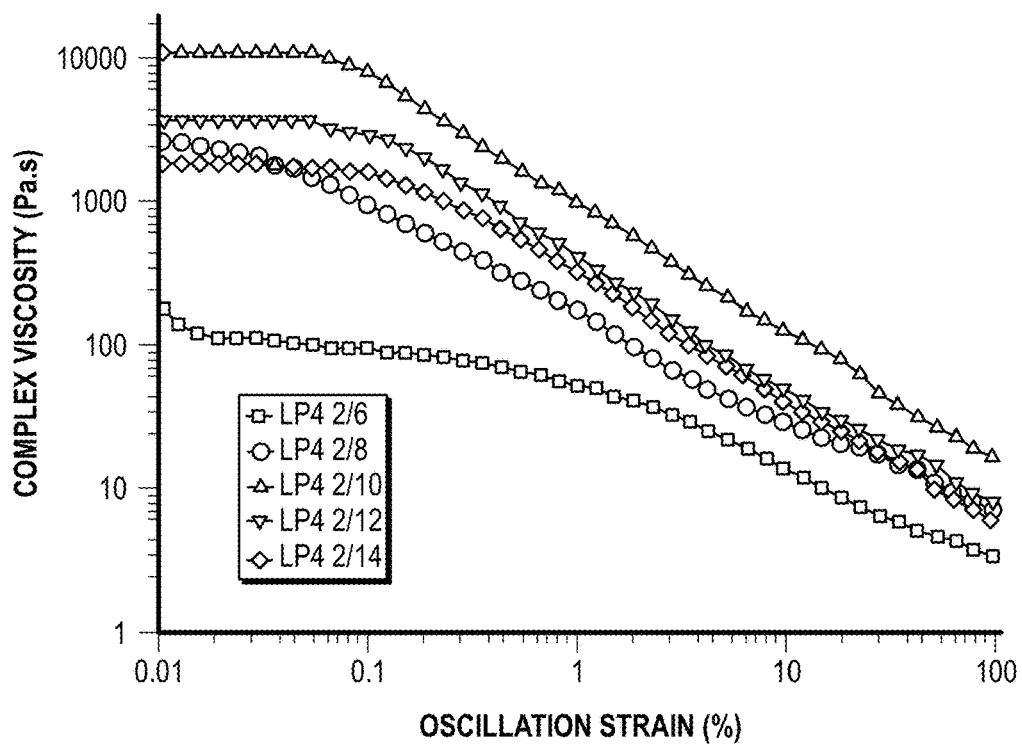
Figure 11D:
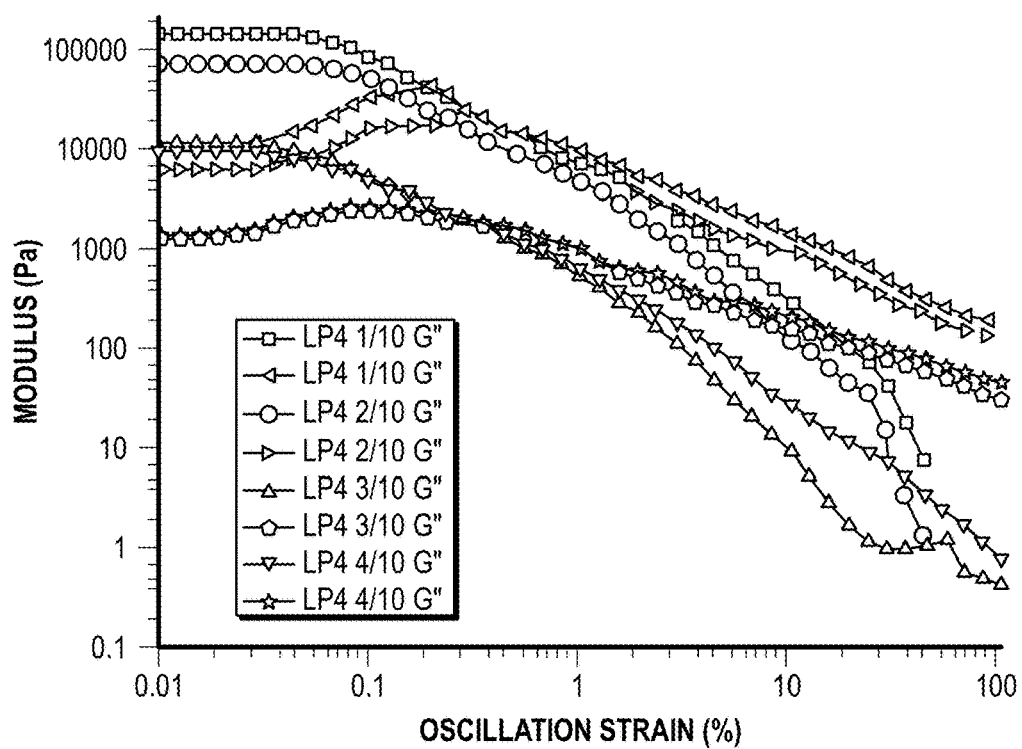
Figure 11E:
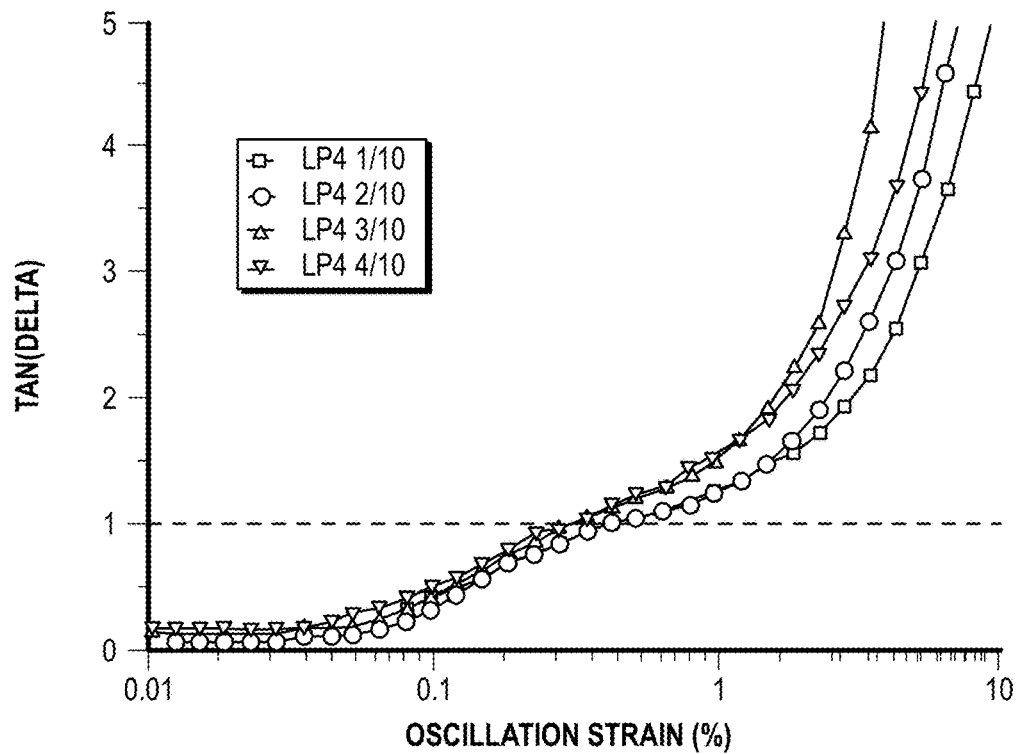
Figure 11F:
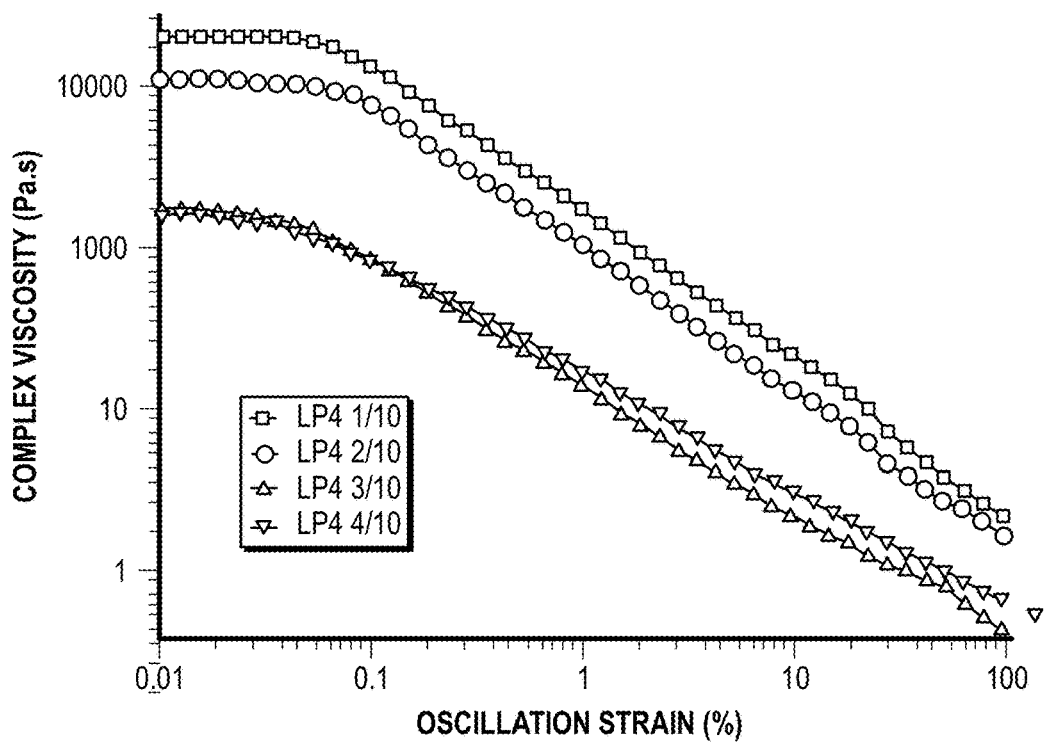

The concentration of α-CD affected the rheological behavior of the hydrogel systems as the polymer influenced the formation of hydrophobic polypseudorotaxanes through supramolecular cross-linking. FIG. 8A and FIG. 8B shows the rheological results of the hydrogels containing different amounts of α-CD (with the same amount of Lig-PEG1, 2%). LP1 2/6 containing only 6% of α-CD showed the lowest G', G" and complex viscosity, and these values increased with the increase of α-CD amount up to a concentration of 10%. FIG. 8C and FIG. 8D shows the rheological properties of the hydrogels with different amounts of Lig-PEG1 (containing the same amount of α-CD, 10%). The concentration of PEGMA also played a significant role in the formation of supramolecular hydrogels. Inadequate PEGMA chains were not able to form a stable hydrogel, but an excess amount of PEGMA (a low α-CD:EG ratio) would result in an unstable network structure and even phase separation. In this study, 0.5% of lignin-PEGMA copolymer was not able to form hydrogel, and 1% (and above) of each copolymer could form a gel after mixing with α-CD. As shown in FIG. 8C and FIG. 8D, LP1 1/10 with 1% copolymer showed the highest G', G" and complex viscosity, and these values exhibited a decreasing trend with the increase in the Lig-PEG1 amount. The explanation might be that the excess amount of copolymers hindered the stacking of the α-CD nanotubes as well as the formation of polypseudorotaxanes. Similar results were also observed in Lig-PEG2 and Lig-PEG4 hydrogels (FIGS. 10A-10C and FIGS. 11A-11F). FIGS. 10A-10C show the dynamic rheological behaviours, such as storage (FIG. 10A), Tan delta (FIG. 10B), and complex viscosity (FIG. 10C), of Lig-PEG2 hydrogels hydrogels under amplitude sweep. FIGS. 11A-11F show the dynamic rheological behaviours, such as storage (FIG. 11A and FIG. 11D); Tan delta (FIG. 11B and FIG. 11E); complex viscosity (FIG. 11C and FIG. 11F), of the Lig-PEG4/α-CD hydrogels under amplitude sweep (oscillation strain from 0.01% to 100%). FIG. 11A to FIG. 11C show the rheological properties of Lig-PEG4 hydrogels with different concentration of α-CD (6% to 14%), and FIG. 11D to FIG. 11F show the rheological properties of the hydrogels with different concentration of Lig-PEG4 (1% to 4%).

Figure 12A:
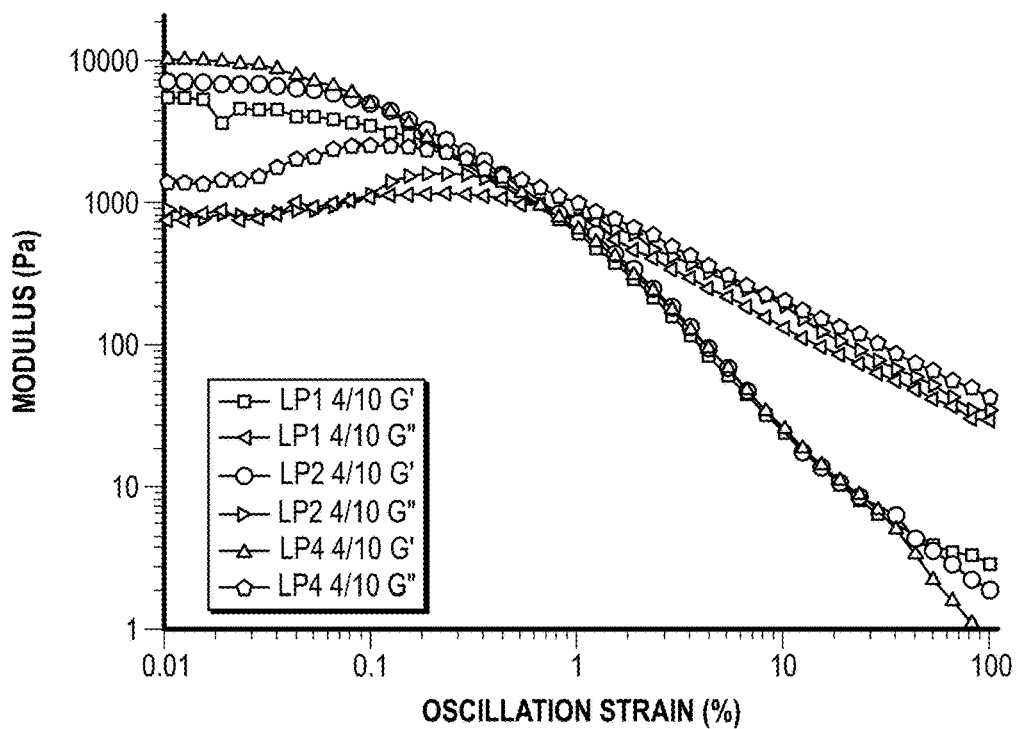
FIGS. 12A-12C
Figure 12B:
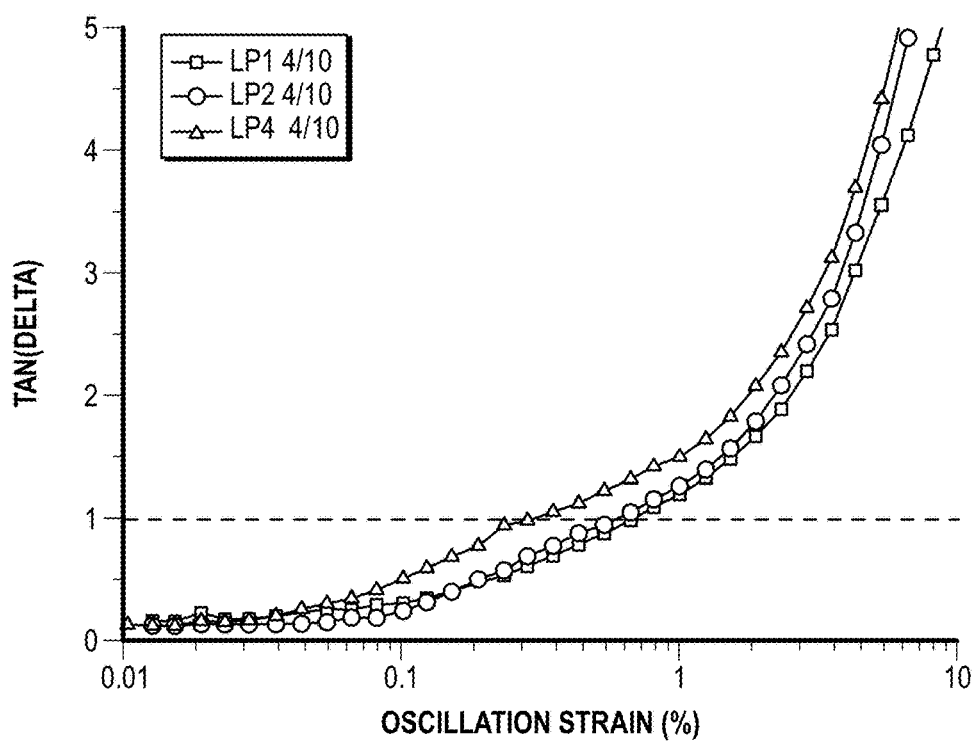
Figure 12C:
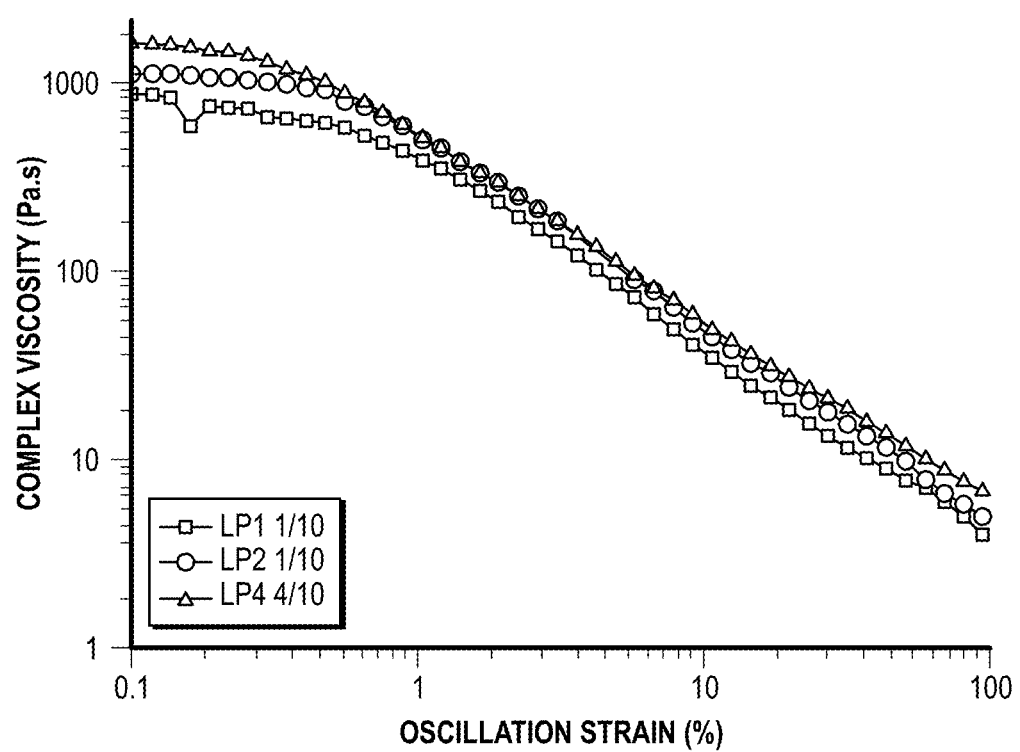

The chain lengths of the PEGMA segments also affected the viscoelastic properties of the hydrogels. FIG. 8E and FIG. 9F shows the rheological properties of the hydrogels made of different copolymers (with the same polymer concentration). The Lig-PEG4 hydrogels exhibited the highest G', G" and complex viscosity, whereas the Lig-PEG1 hydrogels displayed the lowest viscoelastic properties. The hydrogels in other concentrations showed the similar trend (FIGS. 12A-12C), which compared the dynamic rheological behaviours (amplitude sweep), such as storage (FIG. 12A); Tan delta (FIG. 12B); complex viscosity (FIG. 12C), of the hydrogel systems made of different copolymers (4% copolymers with 10% α-CD)). By increasing the ratio of PEGMA in the copolymers, this increased the cross-linking density and enhanced the moduli and viscosity of the hydrogels. The results here indicated that the viscoelastic properties of the mechanically responsive lignin hydrogels were easily tunable by adjusting the copolymer concentrations, α-CD concentrations, or even the molecular weights of the PEGMA segments.

Figure 13A:
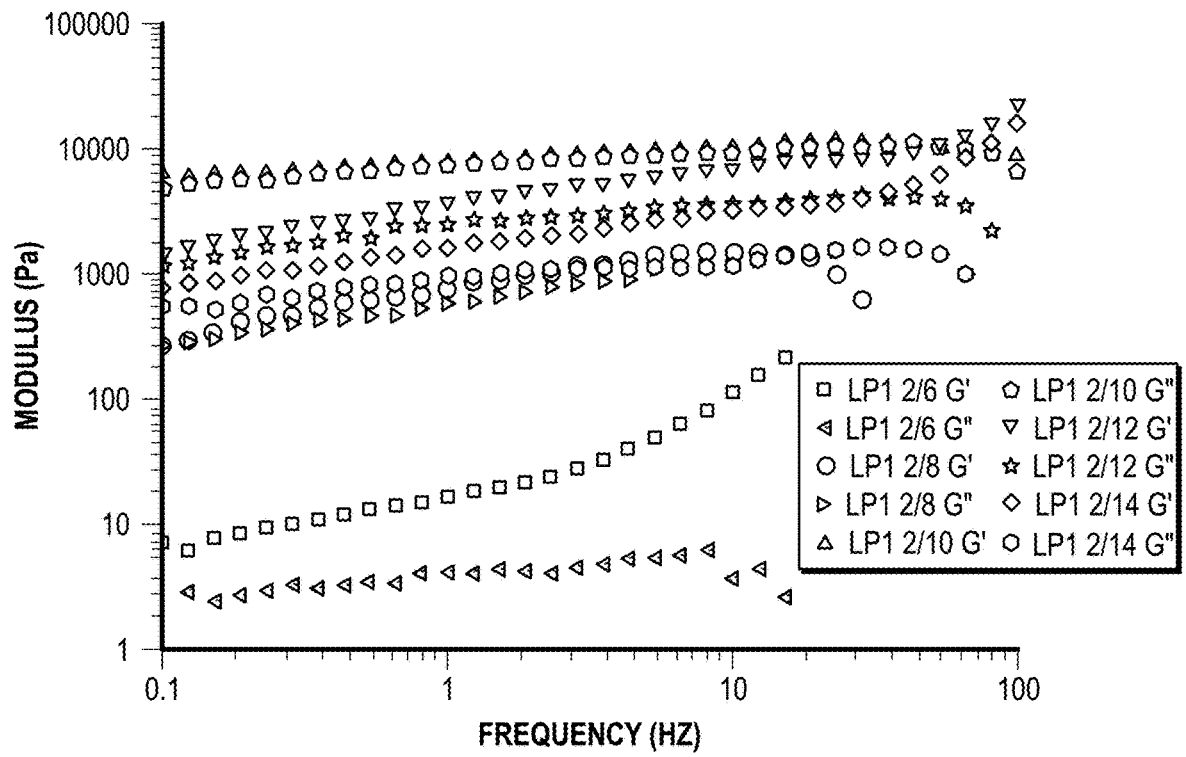
FIGS. 13A-13C
Figure 13B:
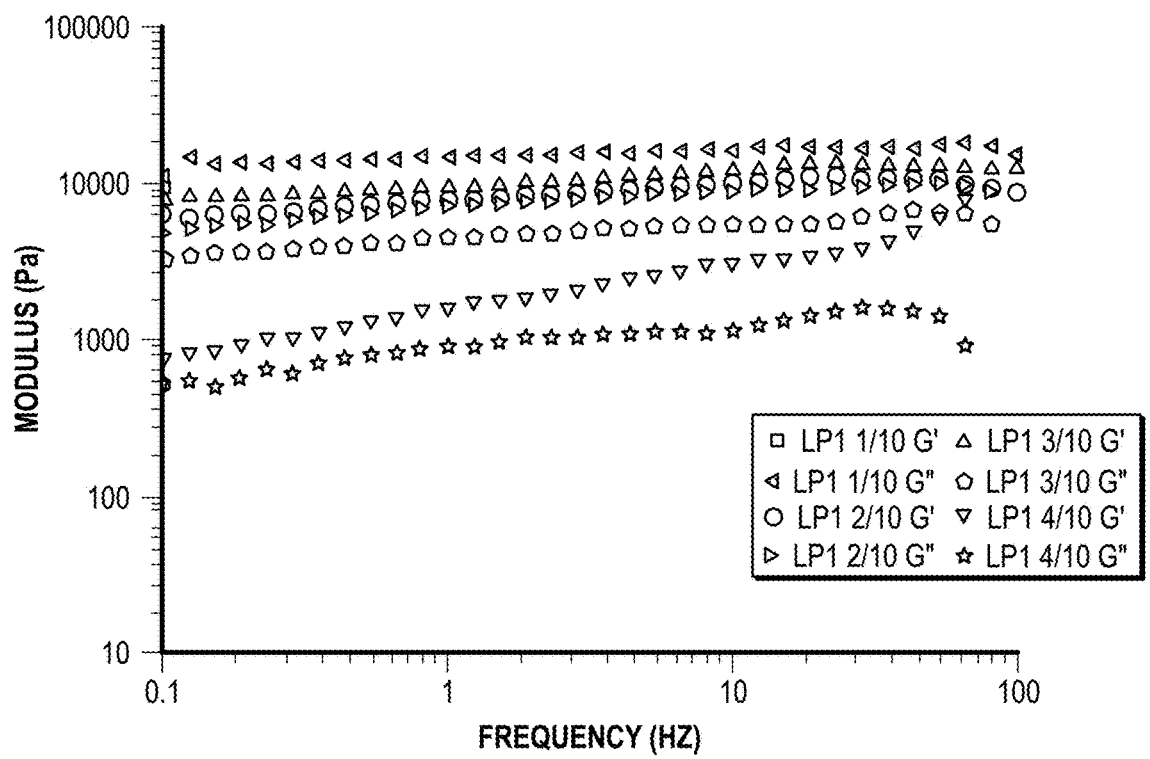
Figure 13C:
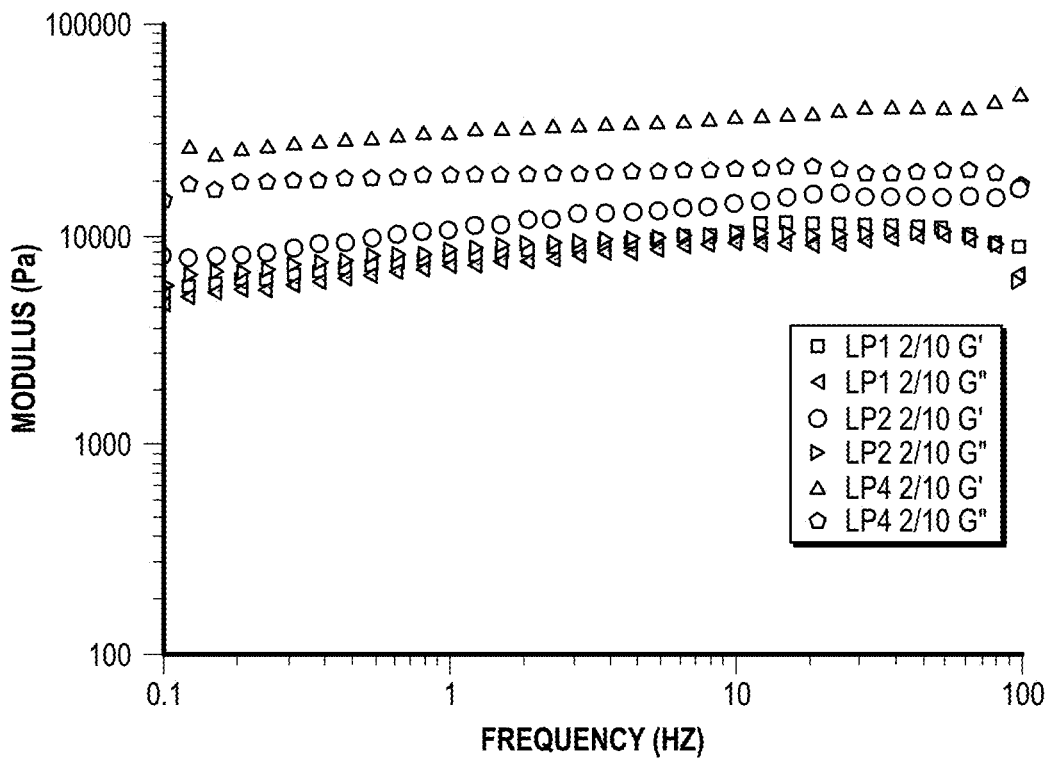
Figure 14A:
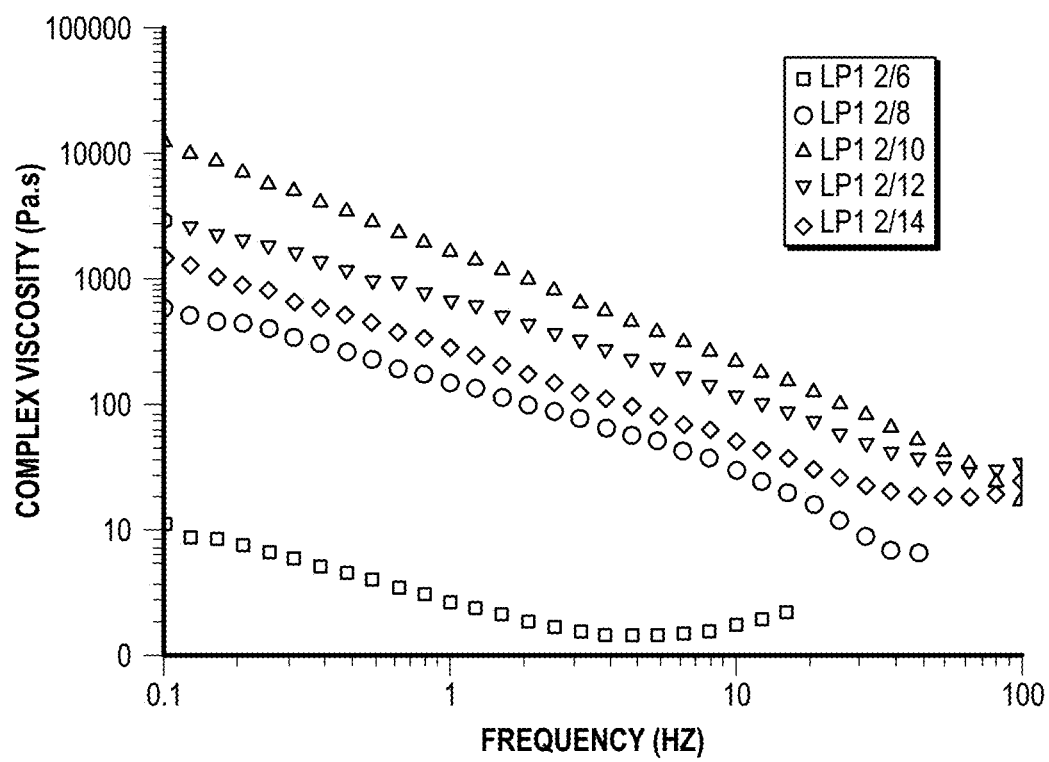
FIGS. 14A-14C
Figure 14B:
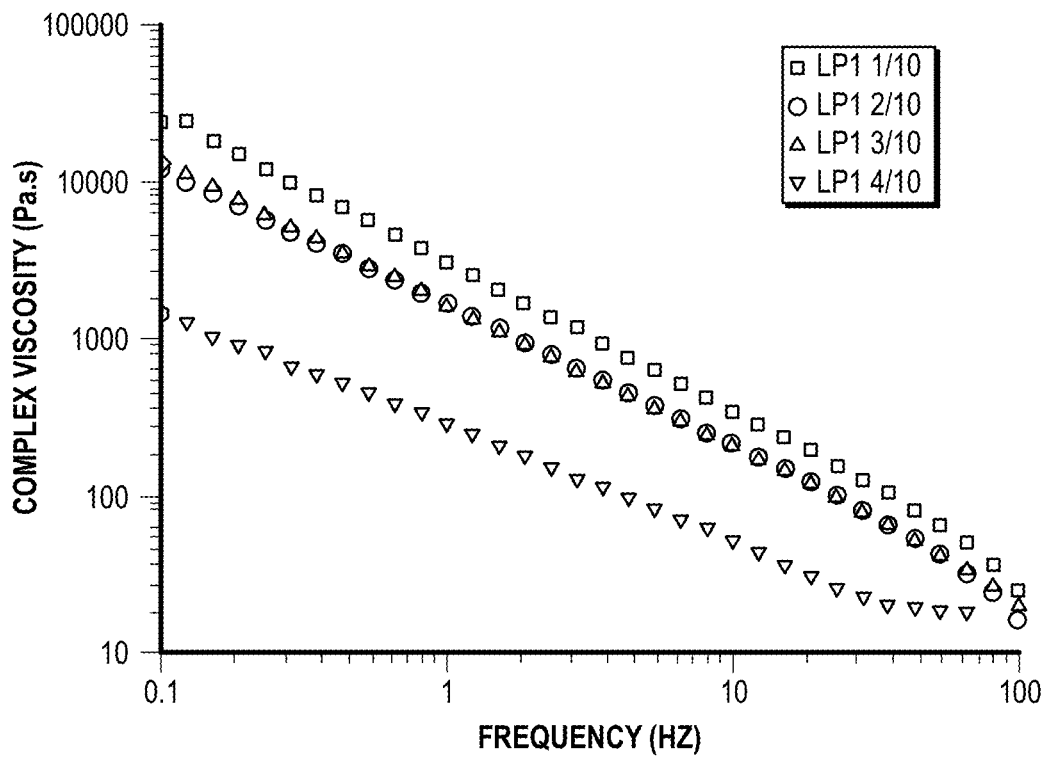
Figure 14C:
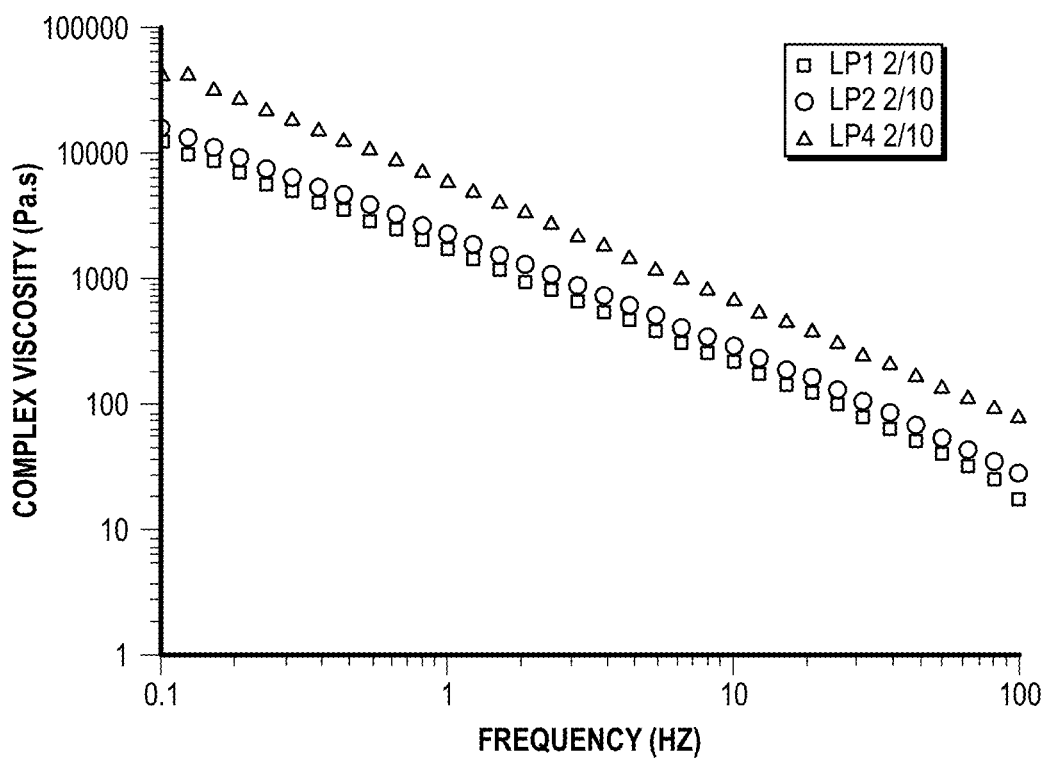

Furthermore, the rheological properties of the hydrogels were characterized by using a frequency sweep at a strain of 0.1%. FIGS. 13A-13C depict the G' and G" of the lignin hydrogels with different polymer concentrations and different types of the copolymers. FIG. 13A shows the dynamic rheological behaviours of lignin PEG1 hydrogels with different concentration of α-CD (6% to 14%), FIG. 13B shows the dynamic rheological behaviours of hydrogels with different concentration of Lig-PEG1 (1% to 4%) and FIG. 13C is a comparison of the dynamic rheological behaviours of the hydrogel systems made of different copolymers. As the strain was only 0.1%, G' of all the hydrogels were dominant over the entire frequency range. It indicated that these hydrogels exhibited a substantial elastic response, possessed a permanent network and displayed strength and rigidity. It was also noted that those stronger hydrogels with higher mechanical properties (G' and G") tended to perform as an elastic solid and showed frequency-independent G', while the weaker systems (such as LP1 2/6, LP1 2/8 and LP1 4/10) showed a changed G' especially at high frequency. As a frequency-dependent G' is related to a fluid-like material or unstable emulsion, those weak hydrogels tended to lose their cross-linked networks under high frequencies. The complex viscosities of all the hydrogels decreased gradually and linearly with the increasing oscillation frequency, confirming that the polymers were dispersed uniformly in the medium and formed stable network systems (FIGS. 14A-14C), which show the complex viscosities of the lignin/α-CD hydrogels under frequency sweep of Lig-PEG1 hydrogels with different concentration of α-CD (6% to 14%) (FIG. 14A), the hydrogels with different concentration of Lig-PEG1 (1% to 4%) (FIG. 14B), and comparison of the complex viscosities of hydrogel systems made of different copolymers (FIG. 14C)).

Example 4

Self-Healing of Lignin/α-CD Hydrogels

The self-healing ability of the lignin/α-CD hydrogels was investigated by assembling the hydrogels at 37° C. and 1 Hz under a small strain of 0.1% for 300 seconds (Step A). After step A, a large strain of 10% was applied for 150 seconds under the same temperature and frequency (Step B). after that, steps A and B were repeated alternatively four times.

Figure 15:
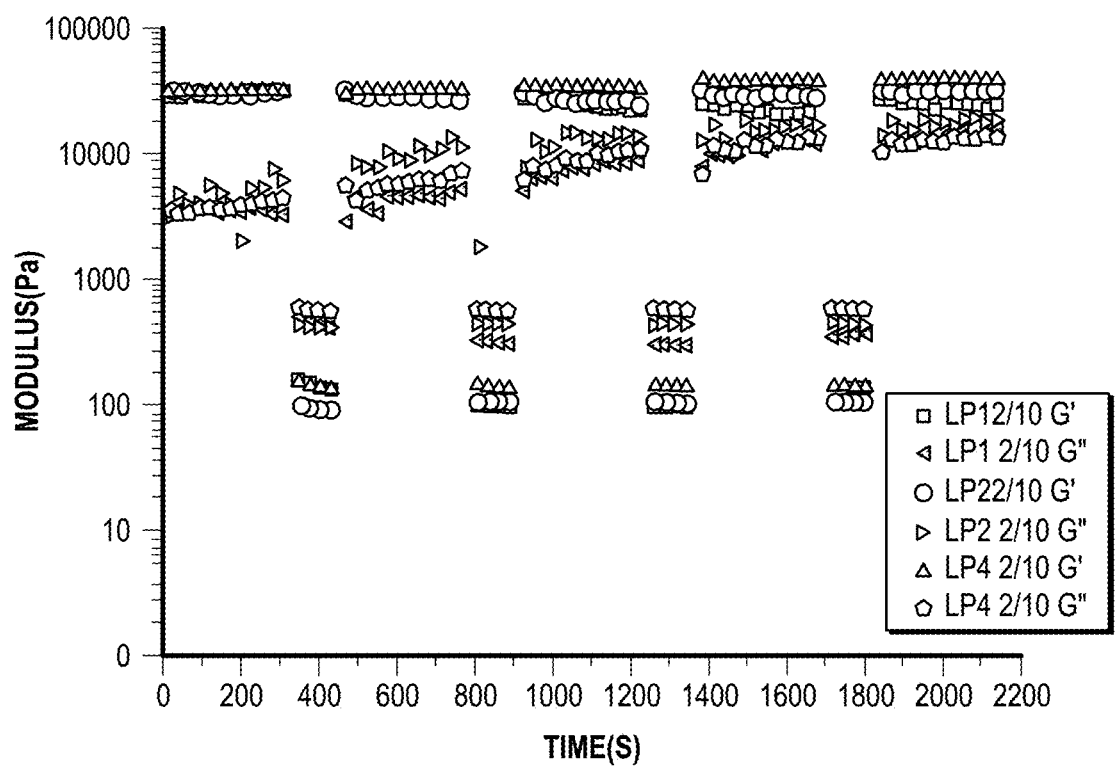
FIG. 15

FIG. 15 shows the typical self-healing curves of LP1 2/10, LP2 2/10 and LP4 2/10 hydrogels (where solid symbols represented storage modulus and open symbols represent loss modulus). All three systems formed gel under 0.01% of oscillation strain (G'>G") at the beginning and G' were constant against time. When the oscillation strain was shifted to 10%, the hydrogel networks were disturbed and the systems failed to form flowable liquid phase with G' below G". After the gels were destroyed for 150 seconds, the low strain of 0.01% was reapplied. When the strain was reduced below the critical strain, the flowable sols rapidly recovered to form gel within 5 seconds. G' became dominant again and returned to their original values as pre-failure. These self-healing behaviors were repeated for at least four cycles, and the systems were always able to recover and form stable hydrogel structures. Among these three hydrogels, LP4 2/10 exhibited the best self-healing capability as its G' always recovered to the same values as before, even after the fourth disturbance. On the other hand, LP1 2/10 and LP2 2/10 showed relatively weaker recoverability as their G' decreased gradually compared to the original values after three cycles. These results suggested that longer chains of PEGMA would improve the self-healing capability of the hydrogels.

Recently, many different self-healing polymeric materials have been designed and reported by utilizing various non-covalent interactions and dynamic covalent bonds as a "binder". The self-healing properties of the lignin supramolecular hydrogels of the present disclosure are based on the reversible host-guest inclusion complexation. Under high strain, the host-guest inclusion disassembles and the hydrogel was broken. When the force was removed, hydrogen bonding between the exteriors of the bound cyclodextrins formed again and led to the reformation of crystalline domains and polymer-chain cross-linking. It is a big advantage that the self-healing process of the lignin supramolecular hydrogels occurs autonomously without any external treatment. This is compared to other types of hydrogels which can take hours to recover or never at all. In comparison, the lignin hydrogel systems of the present disclosure only took a few seconds to recover to the value before, as the lignin copolymers with multiple PEGMA side chains enhanced the host-guest interaction and accelerated the cross-linking of the supramolecular networks.

Example 5

Cytotoxicity of Lignin-PEGMA Copolymers

MTT assays were performed to assess the metabolic activity of human dermal fibroblasts. Human dermal fibroblasts were seeded in 96-well plates (Costar, USA) at a density of $1 \times 10^4$ cells/mL. After 24 hours of incubation, the medium was replaced by the Lig-PEG1, Lig-PEG2, Lig-PEG4, α-CD and P(PEGMA) (Mn=18 000 g/mol) aqueous solutions at concentrations of 10 μM, 5 μM and 1 μM, respectively. The cells were then incubated for 24 hours, 48 hours and 72 hours, respectively. After the designated time intervals, the wells were washed twice with 1×PBS buffer, and 100 μL of freshly prepared MTT (0.5 mg/mL) solution in culture medium was added to each well. The MTT medium solution was carefully removed after 3 hours incubation in the incubator. DMSO (100 μL) was then added into each well, and the plate was gently shaken for 10 minutes at room temperature to dissolve all precipitates formed. The absorbance of MTT at 570 nm was monitored by the microplate reader (Genios Tecan, Switzerland). Cell viability was expressed by the ratio of absorbance of the cells incubated with polymer solution to that of the cells incubated with culture medium only.

Figure 16A:
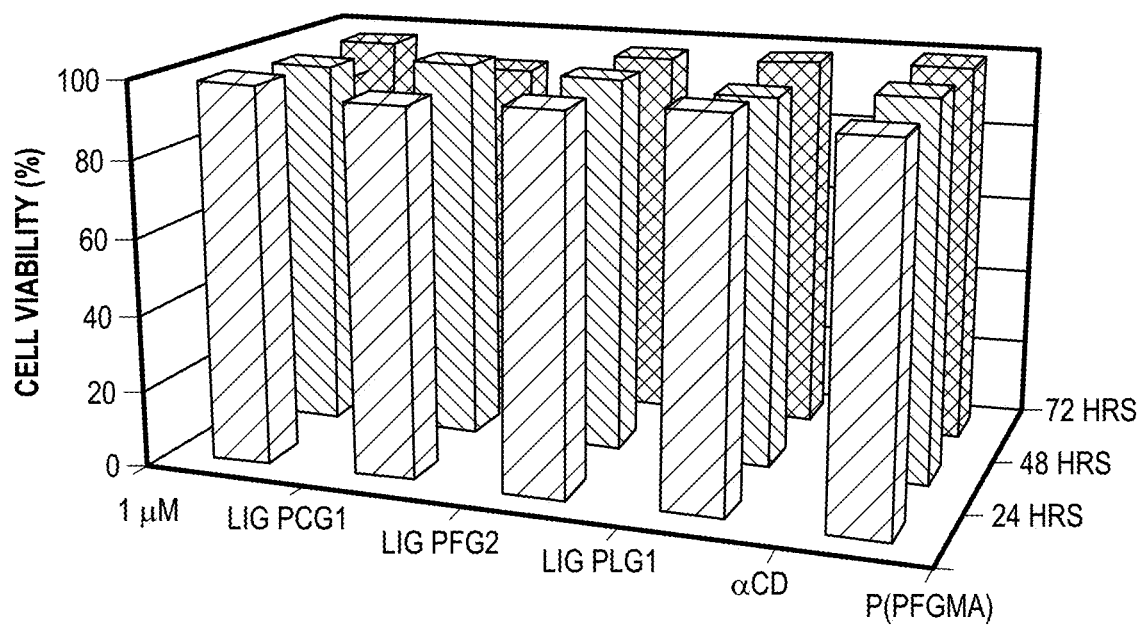
FIGS. 16A-16C
Figure 16B:
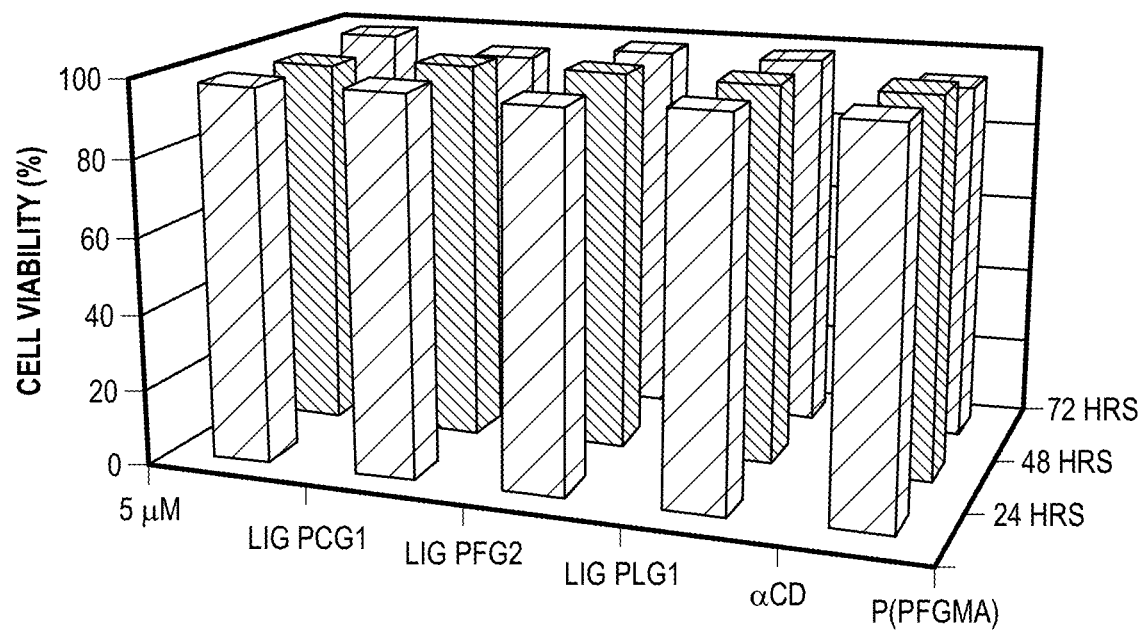
Figure 16C:
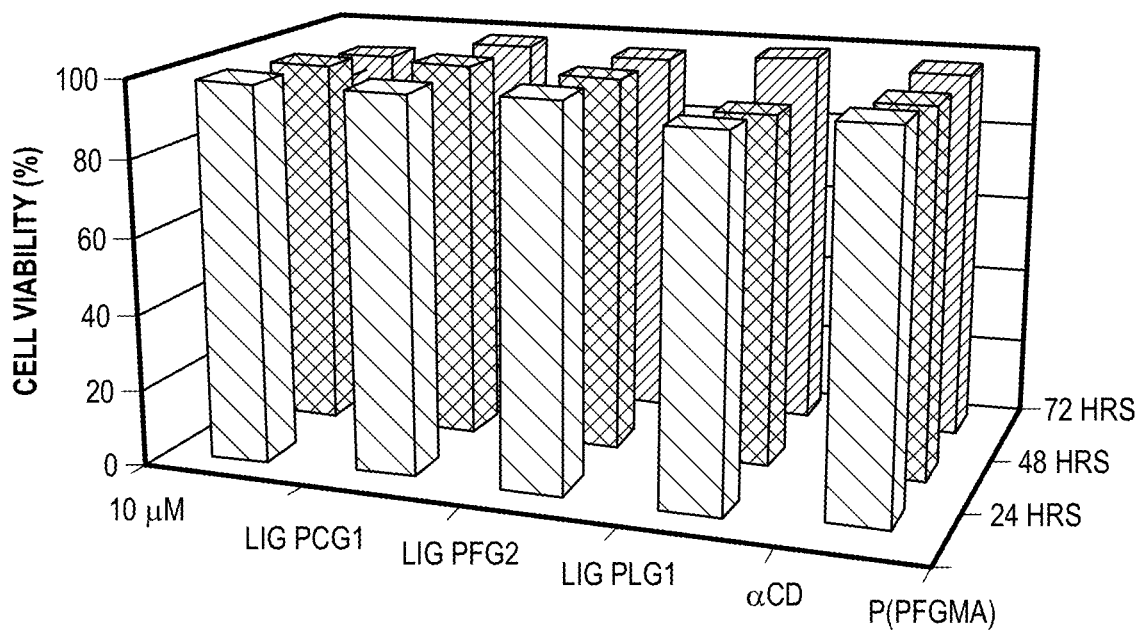

All of the lignin-PEGMA copolymers exhibited excellent cell viability (>95%) even at 10 μM (FIGS. 16A-16C, where FIG. 16A is based on 1 μM, FIG. 16B is based on 5 μM, and FIG. 16C is based on 10 μM concentrations against human dermal fibroblasts for 24 hours, 48 hours and 72 hours). With the similar cell viability to that of P(PEGMA), it is suggested that lignin in the copolymers had no cytotoxicity to the fibroblasts.

It was also found that even after 72 hours of culture, the cells still exhibited high metabolic activity within the polymers solutions. As both the lignin-PEGMA copolymers and α-CD showed no cytotoxicity to the human cells, it can be concluded that the lignin-based supramolecular hydrogels of the present disclosure are biocompatible and are able to be used as biomaterials for multiple biomedical or health-care applications.

INDUSTRIAL APPLICABILITY

The copolymer comprising an oxygenated polyaromatic alcohol and a poly (alkylene oxide) alkyl ether (meth) acrylate may be biodegradable, sustainable and environment-friendly. The molecular weight and thermal properties of the copolymer may be tunable. Thus, the copolymer may potentially be used as an alternative for petroleum-based polymers.

The copolymer may be used to form a hydrogel, the hydrogel may be an injectable hydrogel with adjustable rheological properties, tunable color tones, excellent mechanically-responsive and/or with self-heal capability. The hydrogel may further comprise a cyclic oligosaccharide as part of the gel-forming composition.

The hydrogel may be formed at an ambient temperature and may require only a low concentration of the copolymer or a low concentration of the cyclic oligosaccharide.

The copolymer may form the core of the hydrogel. The oxygenated polyaromatic alcohol of the copolymer may be biodegradable or biocompatible, while the poly (alkylene oxide) alkyl ether (meth)acrylate of the copolymer may be easily recyclable or excreted from a body (if ingested by a human/animal), such that the entire hydrogel can be biodegradable.

The hydrogel can be used in biomedical or personal care industries. The hydrogel may be used as a vehicle to carry an active ingredient (such as a therapeutic or nutritional agent) into a body. The hydrogel maybe used as a sustained delivery vehicle or a controlled delivery vehicle. The hydrogel may be used to reconstitute weakened or damaged parts of a body, such as wound healing or to repair a joint. The hydrogel may be used in hair products, such as in hair gel, or in a cosmetic product. The hydrogel may be used as a tissue engineering scaffold.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A hydrogel comprising:
   1 wt % to 4 wt % of a copolymer comprising an oxygenated polyaromatic alcohol and a poly (alkylene oxide) alkyl ether (meth)acrylate; and
   6 wt % to 14 wt % of a cyclic oligosaccharide.
2. The hydrogel of claim 1, wherein said copolymer has a molecular weight in the range of 5,000 g/mol to 500,000 g/mol.
3. The hydrogel of claim 1, wherein said copolymer has a polydispersity of at least 1.
4. The hydrogel of claim 1, wherein said copolymer has a melting temperature in the range of 32° C. to 36° C.
5. The hydrogel of claim 1, wherein said copolymer has a degradation temperature in the range of 350° C. to 370° C.
6. The hydrogel of claim 1, wherein said copolymer has 5 to 1,000 molecules of poly (alkylene oxide) alkyl ether (meth)acrylate bound to each molecule of the oxygenated polyaromatic alcohol.
7. The hydrogel of claim 1, wherein said oxygenated polyaromatic alcohol is a lignin or a lignin derivative,
   wherein said lignin is selected from the group consisting of lignin, steam explosion lignin, acid hydrolysis lignin, lignosulfonate, soda lignin and organosolv lignin or
   wherein said lignin derivative is selected from the group consisting of lignin esters, lignin ethers, carboxy lignins, hydroxyalkylated lignin, acylated lignin and hydroxyalkoxy lignins or is further selected from the group consisting of lignin acetate, lignin propionate, lignin butyrate, lignin ethyl ether, lignin methyl ether, carboxymethyl lignin, (hydroxyethoxy) lignin, and (hydroxypropoxy) lignin.
8. The hydrogel of claim 1, wherein said oxygenated polyaromatic alcohol is contained in said copolymer at a weight percentage in the range of 0.5% to 90%.
9. The hydrogel of claim 1, wherein said poly (alkylene oxide) alkyl ether (meth)acrylate is selected from the group consisting of poly (ethylene glycol) methyl ether (meth) acrylate, poly (ethylene glycol) ethyl ether (meth)acrylate, poly (propylene glycol) methyl ether (meth)acrylate, poly (propylene glycol) ethyl ether (meth)acrylate, and mixtures thereof.
10. The hydrogel of claim 1, wherein said poly (alkylene oxide) alkyl ether (meth)acrylate is a grafted polymer, a block copolymer, a star polymer, a brush polymer or a hyperbranched polymer.
11. The hydrogel of claim 1, wherein said poly (alkylene oxide) alkyl ether (meth) acrylate contains an average number of alkylene oxide groups in the range of from 2 to 460.
12. The hydrogel of claim 1, wherein said poly (alkylene oxide) alkyl ether (meth)acrylate has a molecular weight in the range of 200 g/mol to 20,000 g/mol.
13. The hydrogel of claim 1, further comprising a polymer selected from the group consisting of polyester, polyurethane, polyamide, polyether, polysaccharide, poly(amino acid)s, polypeptides and proteins.
14. The hydrogel of claim 1 wherein the cyclic oligosaccharide is selected from the group consisting of α-cyclodextrin, β-cyclodextrin, γ-cyclodextrin and methyl-β-cyclodextrin.
15. The hydrogel of claim 1, having a storage modulus in the range of 0.01 Pa to 100 GPa.
16. A method for forming a hydrogel comprising adding a cyclic oligosaccharide to a copolymer to form a mixture that undergoes gelation to form the hydrogel, wherein said copolymer comprises an oxygenated polyaromatic alcohol and a poly (alkylene oxide) alkyl ether (meth)acrylate, and wherein the formed hydrogel comprises about 1 wt % to about 4 wt % of said copolymer and about 6 wt % to about 14 wt % of said cyclic oligosaccharide.
17. The method of claim 16, wherein said mixture is 1) a copolymer aqueous solution mixed with a cyclic oligosaccharide aqueous solution, or 2) the cyclic oligosaccharide in powder form added to a copolymer aqueous solution.
18. The method of claim 17, wherein said copolymer aqueous solution comprises 0.1 wt % to 80 wt % of said copolymer, based on the weight of the mixture.

19. The method of claim 16, wherein the mixture contains 1 wt % to 50 wt % of the cyclic oligosaccharide, based on the weight of the mixture.

\* \* \* \* \*